(12) United States Patent
Zhang et al.

(10) Patent No.: US 9,856,509 B2
(45) Date of Patent: Jan. 2, 2018

(54) FLUORESCENT SUBSTRATES FOR DETERMINING LYSINE MODIFYING ENZYME ACTIVITY

(71) Applicant: The Broad Institute, Inc., Cambridge, MA (US)

(72) Inventors: Yan-Ling Zhang, Lexington, MA (US); Edward Holson, Newton, MA (US); Florence F. Wagner, Ashland, MA (US)

(73) Assignee: The Broad Institute, Inc., Cambridge, MA (US)

( * ) Notice: Subject to any disclaimer, the term of this patent is extended or adjusted under 35 U.S.C. 154(b) by 425 days.

(21) Appl. No.: 14/267,276

(22) Filed: May 1, 2014

(65) Prior Publication Data
US 2014/0335550 A1 Nov. 13, 2014

Related U.S. Application Data

(63) Continuation of application No. PCT/US2012/063377, filed on Nov. 2, 2012.

(60) Provisional application No. 61/628,562, filed on Nov. 2, 2011.

(51) Int. Cl.
| | | |
|---|---|---|
| *C12Q 1/34* | (2006.01) | |
| *C09K 11/06* | (2006.01) | |
| *C12Q 1/37* | (2006.01) | |
| *C07K 7/06* | (2006.01) | |
| *C07K 5/10* | (2006.01) | |
| *C07D 311/82* | (2006.01) | |
| *C12N 9/14* | (2006.01) | |

(52) U.S. Cl.
CPC .............. *C12Q 1/34* (2013.01); *C07D 311/82* (2013.01); *C07K 5/10* (2013.01); *C07K 7/06* (2013.01); *C09K 11/06* (2013.01); *C12Q 1/37* (2013.01); *C09K 2211/1007* (2013.01); *C09K 2211/1088* (2013.01); *G01N 2333/98* (2013.01)

(58) Field of Classification Search
CPC .......... C12Q 1/34; C12Q 1/37; C07D 311/82; C07K 5/10; C07K 7/06; C09K 2211/1007; C09K 2211/1088; C09K 11/06; G01N 2333/98
See application file for complete search history.

(56) References Cited

U.S. PATENT DOCUMENTS

| | | | |
|---|---|---|---|
| 2004/0018579 A1* | 1/2004 | Cook | G01N 33/542 435/23 |
| 2004/0091951 A1* | 5/2004 | Schultz | C07C 259/10 435/7.92 |
| 2007/0087400 A1 | 4/2007 | Darzins et al. | |
| 2008/0293081 A1 | 11/2008 | Milne et al. | |
| 2016/0060679 A1 | 3/2016 | Holson et al. | |

FOREIGN PATENT DOCUMENTS

| | | |
|---|---|---|
| GB | 2459976 A | 11/2009 |
| WO | 02/12267 A1 | 2/2002 |
| WO | 2010/092381 A1 | 8/2010 |
| WO | 2010/121023 A2 | 10/2010 |
| WO | 2011/019393 A2 | 2/2011 |

OTHER PUBLICATIONS

Wegener, D; Wirsching, F; Riester, D; and Schwienhorst, A "A Fluorogenic Histone Deacetylase Assay Well Suited for High-Throughput Activity Screening" Chemistry & Biology, vol. 10, 61-68, Jan. 2003.*
Hu, M., et al., "Supporting Information: Multi-Color, One-and Two-Photon Imaging of Enzymatic Activities in Live Cells with Fluorescently Quenched Activity-Based Probes (qABPs)," J. Am. Chem. Soc., 133(31): 12009-12020 (2011).
Jiskoot, W., et al., "Preparation and Application of a Fluorescein-Labeled Peptide for Determining the Affinity Constant of a Monoclonal Antibody-Hapten Complex by Fluorescence Polarization," Anal. Biochem., 196(2): 421-426 (1991).
Dumelin, C. E., et al., "A Portable Albumin Binder from a DNA-Encoded Chemical Library," Angew. Chem. Int. Ed., 47(17): 3196-3201 (2008).
Ikeda, M., et al., "Development of a DNA-binding TEMPO derivative for evaluation of nuclear oxidative stress and its application in living cells," Free Radical Biology and Medicine, 49(11): 1792-1797 (2010).
Wollack, J. W., et al., "Multifunctional Prenylated Peptides for live Cell Analysis," J. Am. Chem. Soc., 131(21): 7293-7303 (2009).
De Waart, D. R., et al., "Hepatic Transport Mechanisms of Cholyl-L-Lysyl-Fluorescein," J. Pharmacol. Exp. Therapeutics, 334(1): 78-86 (2010).
Mills, C. O., et al., "Different pathways of canalicular secretion of sulfated and non-sulfated fluorescent bile acids: a study in isolated hepatocyte couplets and TR-rats," J. Hepatology, 31(4): 678-684 (1999).
Lohse, J., et al., "Fluorescein-Conjugated Lysine Monomers for Solid Phase Synthesis of Fluorescent Peptides and PNA Oligomers," Bioconj. Chem., 8(4): 503-509 (1997).

* cited by examiner

*Primary Examiner* — Chris R Tate
*Assistant Examiner* — Aaron J Kosar
(74) *Attorney, Agent, or Firm* — Elmore Patent Law Group, P.C.; Mahreen Hoda; Carolyn Elmore

(57) ABSTRACT

The invention relates to a compound of Formula I:

$$F_1-X_1-L_1-X_2-P_1-X_3-G_1 \quad \text{(Formula I)}.$$

29 Claims, 10 Drawing Sheets

| HDAC Enzyme | Broad Substrate A | | | H218 | | |
|---|---|---|---|---|---|---|
| | HDAC Concentration | Reaction time | Substrate Conversion | HDAC Concentration | Reaction time | Substrate Conversion |
| HDAC1 | 5nM | 1HR | 27% | 200nM | 3HR | 18% |
| HDAC2 | 3nM | 1HR | 20% | 200nM | 5HR | 20% |
| HDAC3 | 5nM | 1HR | 30% | 20nM | 1HR | 30% |

| HDAC Enzyme | Broad Substrate A Kca/Km ($M^{-1}s^{-1}$) | Broad Substrate E Kca/Km ($M^{-1}s^{-1}$) |
|---|---|---|
| HDAC1 | $1.5 \times 10^4$ | <14 |
| HDAC2 | $1.8 \times 10^4$ | <14 |
| HDAC3 | $1.7 \times 10^4$ | $7 \times 10^2$ |

FIG. 2

| HDAC Enzyme | Substrate | HDAC Concentration (nM) | Substrate Conversion% @1hr |
|---|---|---|---|
| HDAC1 | Substrate A | 5 | 27% |
| HDAC2 | Substrate A | 3 | 20% |
| HDAC3 | Substrate A | 5 | 30% |
| HDAC4 | Substrate B | 0.5 | 38% |
| HDAC5 | Substrate B | 1 | 17% |
| HDAC6 | Substrate A | 2 | 29% |
| HDAC7 | Substrate B | 0.5 | 45% |
| HDAC8 | Substrate B | 0.5 | 22% |
| HDAC9 | Substrate B | 1 | 25% |

FIG. 3

| HDAC Enzyme | LBH-589 | SAHA | CI-994 | BRD6929 |
|---|---|---|---|---|
| HDAC1 | <0.005 | 0.008 | 0.5 | 0.02 |
| HDAC2 | <0.003 | 0.030 | 0.7 | 0.05 |
| HDAC3 | <0.005 | 0.007 | 0.6 | 3.7 |
| HDAC4 | 0.065 | >30 | >30 | >30 |
| HDAC5 | 0.022 | 18 | >30 | >30 |
| HDAC6 | 0.002 | 0.002 | >30 | >30 |
| HDAC7 | 0.76 | >30 | >30 | >30 |
| HDAC8 | 0.025 | 0.72 | >30 | >30 |
| HDAC9 | 0.39 | >30 | >30 | >30 |

FIG. 4

|  | Substrate A | | | H218 | | |
|---|---|---|---|---|---|---|
| HDAC Enzyme | SAHA | CI-994 | BRD6929 | SAHA | CI-994 | BRD6929 |
| HDAC1 | 0.008 | 0.5 | 0.02 | 0.012 | 0.16 | 0.01 |
| HDAC2 | 0.030 | 0.7 | 0.05 | 0.06 | 0.7 | 0.05 |
| HDAC3 | 0.007 | 0.6 | 3.7 | 0.007 | 0.5 | 2.3 |

FIG. 5

HDAC Activity with Microfluidic Mobility-Shift Assays with Broad Substrate A

FLUORESCENT SUBSTRATES FOR DETERMINING LYSINE MODIFYING ENZYME ACTIVITY

RELATED APPLICATIONS

This application is a continuation of International Application No. PCT/US2012/063377, which designated the United States and was filed on Nov. 2, 2012, published in English, which claims the benefit of U.S. Provisional Application No. 61/628,562, filed on Nov. 2, 2011. The entire teachings of the above applications are incorporated herein by reference.

BACKGROUND

Lysine acetylation and deacetylation play important roles in the modulation of chromatin topology and the regulation of gene transcription. Lysine deacetylases and histone deacetylases in particular are proven drug targets for cancer and also potential targets for neurological diseases. A commonly used assay for HDAC activity is a trypsin coupled fluorogenic assay. This indirect endpoint assay is simple and applicable for high throughput screening. However, it is limited in its ability to continuously monitor enzyme activity due to protein's stability in the presence of trypsin. In addition, trypsin inhibitors may impair the assay results. Recently, Caliper microfluidic lab-on-a-chip technology has been used to measure HDAC activity and characterize HDAC inhibitors. This assay directly follows the separated fluorophore-labeled substrate and product using FAM labeled acetylated peptide. Advantages of this direct assay include its ability to continuously monitor enzyme activity and the ability to determine enzyme activity in the absence of trypsin or other proteases which may degrade protein components within the assay. Interference from fluorescent compounds is minimized in screening. This assay is currently limited for a few HDACs such as HDAC3 and 6 due to the lack of efficient HDAC substrates for other HDAC isoforms including HDAC1 and 2. As such, substrates used to determine the activity of all HDAC isoforms using the microfuidic lab-on-chip technology is needed.

SUMMARY OF THE INVENTION

The invention relates to fluorescent conjugates of Formula I:

$$F_1\text{—}X_1\text{-}L_1\text{-}X_2\text{—}P_1\text{—}X_3\text{-}G_1 \quad \text{(Formula I)}$$

wherein $F_1$ is a fluorophore; preferably a fluoresceine based fluorophore; more preferably, 6-carboxy fluorescein (6-FAM);
$L_1$ is alkyl, substituted alkyl, alkenyl, substituted alkenyl, alkynyl, substituted alkynyl, —O—, —S—, —[C($R_{10}$)($R_{11}$)]$_t$—, —N($R_{10}$)—, —N($R_{10}$)[C($R_{10}$)($R_{11}$)]$_t$—, —O[C($R_{10}$)($R_{11}$)]$_t$—, —O[C($R_{10}$)($R_{11}$)C($R_{10}$)($R_{11}$)O]$_u$— or —S[C($R_{10}$)($R_{11}$)]$_t$-aliphatic or substituted aliphatic;
wherein t is 0, 1, 2, 3, 4, 5, 6, 7, 8, 9, 10, 11, 12, 13, 14, 15, 16, 17, 18, 19, 20, 21, 22, 23 or 24;
u is an integer between 1 and 500;
each $R_{10}$ and $R_{11}$ is independently hydrogen, halogen, —O$R_{20}$, —S$R_{20}$, —N$R_{20}R_{21}$, —CF$_3$, —CN, —NO$_2$, —N$_3$, —C(O)O$R_{20}$, —C(O)$R_{20}$, —C(O)N$R_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two of $R_{10}$ and $R_{11}$ groups together with the atoms to which they are attached and any intervening atoms may form an additional optionally substituted, 3, 4, 5, 6 or 7 membered ring;
wherein each $R_{20}$ and $R_{21}$ is independently hydrogen, aliphatic, substituted aliphatic, aromatic or substituted aromatic;
$P_1$ is a peptide or protein that can act as a substrate for an enzyme that modifies a lysine or substituted lysine residue, preferably a lysine deacetylase, which include but are not limited to NAD+-dependent sirtuins (SIRT) and zinc dependent histone deacetylase (HDAC), or lysine acetyltransferase, preferably a histone acetyltransferase; $P_1$ is preferably a one, two, three, four, five, six, seven, eight, nine, ten, eleven, twelve, thirteen, fourteen, fifteen, sixteen, seventeen, eighteen, nineteen, twenty, twenty-one or twenty-two amino acid peptide containing a lysine residue wherein the side chain of the lysine residue is unsubstituted, acetylated or trifluoroacetylated, preferably comprising of natural amino acids, with optional additional substitution; more preferably, a two, three four five or six amino acid peptide comprising natural amino acids with optional additional substitution; more preferably said two, three, four, five or six amino acid peptide is a peptide comprised of natural amino acids, containing an unsubstituted side-chain lysine residue (K) that can be acetylated or a side-chain acetylated lysine residue (K(Ac)) or a side-chain trifluoroacetylated lysine residue (K(COCF$_3$) that can be deacetylated by a HDAC enzyme, or trifluoroacetyl substituted lysine residue that can act as a substrate for HDAC enzyme; more preferably, $P_1$ is a peptide having the sequence of AA$_1$-AA$_2$-AA$_3$-AA$_4$-Lys(Ac) (SEQ ID NO: 2), AA$_1$-AA$_2$-AA$_3$-AA$_4$-Lys(COCF$_3$) (SEQ ID NO: 3), or AA$_1$-AA$_2$-AA$_3$-AA$_4$-Lys (SEQ ID NO: 1) wherein each AA$_1$, AA$_2$ and AA$_3$ is absent or a natural or unnatural amino acid, and AA$_4$ is a natural or unnatural amino acid;
$G_1$ is hydrophobic group;
Preferably, $G_1$ is an optionally substituted alkyl, optionally substituted alkenyl, optionally substituted alkynyl, optionally substituted aryl, optionally substituted heteroaryl group, an alkyl group substituted with an optionally substituted aryl or heteroaryl group, an alkenyl group substituted with an optionally substituted aryl or heteroaryl group or a natural or unnatural amino acid;
Wherein each $X_1$, $X_2$, and $X_3$ is independently a direct bond, —O—, —S—, —C(O)—, —C(O)—NR$_{100}$—, —C(S)—, —C(S)—NR$_{100}$—, —C(O)O—, —NR$_{100}$— and —S(O)$_2$—; wherein $R_{100}$ is hydrogen, alkyl, substituted alkyl, aryl or substituted aryl.

The invention further relates to the use of compound of Formula I for the determination of histone deacetylase activity. The compounds of Formula I can be used to determine the activity of HDAC isoforms 1, 2, 3, 4, 5, 6, 7, 8, 9, 10, 11 or SIRT 1, 2, 3, 4, 5, 6 or 7. In one embodiment, these substrates allow the measurement of activity of full length or truncated variants of histone deacetylases (HDAC 1-11 or SIRT 1-7) and their corresponding complexes with microfluidic lab-on-chip technology. In addition, these substrates can be used for screening HDAC inhibitors, studying mechanism of inhibition and profiling their selectivity. Without being bound to any theory it is postulated that peptide, $P_1$, with C-terminal $G_1$ is a much more efficient HDAC substrate than the conjugate without $G_1$. By conjugating $G_1$ to $P_1$ its specific activity can be increased, for example by more than 100 fold, for acetylated lysine containing peptide substrate. The increased activity can lead to the reduced use of enzymes to reach the desired amount of substrate conversion.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2: Comparison of Coumarine effect on substrate specificity/efficiency.

FIG. 3: % Substrate conversion by HDAC 1-9 using Broad Substrate A and Broad Substrate B.

FIG. 4: Determination of $IC_{50}$ (µM) values for control compounds with no preincubation on HDAC 1-9 using Broad Substrates.

FIG. 5: Comparison of known HDAC inhibitors $IC_{50}$ (µM) values with no preincubation (SAHA, CI-994, BRD6929) using Broad Substrate A vs. commercial substrate.

DETAILED DESCRIPTION OF THE INVENTION

Figure 1:
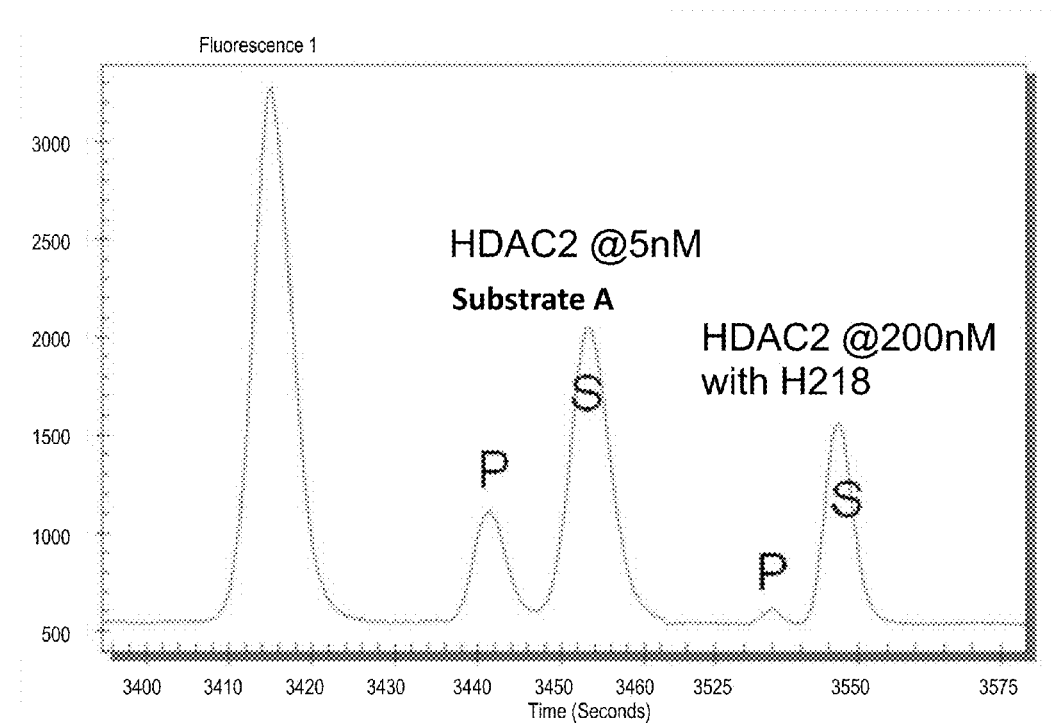
FIG. 1: Comparison of HDAC 1,2,3 activity with Broad Substrate A vs. commercial substrate (H218).

The invention relates to fluorescent conjugates of Formula I:

$$F_1-X_1-L_1-X_2-P_1-X_3-G_1 \quad \text{(Formula I)}$$

Wherein $F_1$ is a fluorophore; preferably a fluoresceine based fluorophore; more preferably, FAM;

$L_1$ is alkyl, substituted alkyl, alkenyl, substituted alkenyl, alkynyl, substituted alkynyl, —O—, —S—, —[C($R_{10}$)($R_{11}$)]$_t$—, —N($R_{10}$)—, —N($R_{10}$)[C($R_{10}$)($R_{11}$)]$_t$—, —O[C($R_{10}$)($R_{11}$)]$_t$—, —O[C($R_{10}$)($R_{11}$)C($R_{10}$)($R_{11}$)O]$_u$— or —S[C($R_{10}$)($R_{11}$)]$_t$-aliphatic or substituted aliphatic;

Wherein t is 0, 1, 2, 3, 4, 5, 6, 7, 8, 9, 10, 11, 12, 13, 14, 15, 16, 17, 18, 19, 20, 21, 22, 23 or 24;

u is an integer between 1 and 500;

Each $R_{10}$ and $R_{11}$ is independently hydrogen, halogen, —O$R_{20}$, —S$R_{20}$, —N$R_{20}R_{21}$, —CF$_3$, —CN, —NO$_2$, —N$_3$, —C(O)O$R_{20}$, —C(O)$R_{20}$, —C(O)N$R_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two of $R_{10}$ and $R_{11}$ groups together with the atoms to which they are attached and any intervening atoms may form an additional optionally substituted, 3, 4, 5, 6 or 7 membered ring;

Wherein each $R_{20}$ and $R_{21}$ is independently hydrogen, aliphatic, substituted aliphatic, aromatic or substituted aromatic;

$P_1$ is a peptide or protein that can act as a substrate to a lysine deacetylase, preferably, a histone deacetylase (HDAC);

$P_1$ is preferably a one, two, three, four, five, six, seven, eight, nine, ten, eleven, twelve, thirteen, fourteen, fifteen, sixteen, seventeen, eighteen or nineteen amino acid peptide containing a lysine residue wherein the side chain of the lysine residue is unsubstituted, acetylated or trifluoroacetylated, more preferably comprising of natural amino acids, with optional additional substitution; preferably, a two, three or four amino acid peptide comprising natural amino acids with optional additional substitution; preferably a peptide containing a side-chain acetylated lysine residue (K(Ac)) that can be deacetylated by a HDAC enzyme, or trifluoroacetyl substituted lysine residue (K(COCF$_3$)) that can act as a substrate for HDAC enzyme, or an unsubstituted side-chain lysine residue (K) that can be acetylated; more preferably, $P_1$ is a peptide having the sequence of $AA_1$-$AA_2$-$AA_3$-$AA_4$-Lys(Ac)—, $AA_1$-$AA_2$-$AA_3$-$AA_4$-Lys or $AA_1$-$AA_2$-$AA_3$-$AA_4$-Lys(COCF$_3$)— wherein each $AA_1$, $AA_2$ and $AA_3$ is absent or a natural or unnatural amino acid, and $AA_4$ is a natural or unnatural amino acid; preferably each $AA_1$, $AA_2$, $AA_3$ or $AA_4$ is independently selected from Isoleucine (I), Alanine (A), Leucine (L), Asparagine (N), Lysine (K), Aspartic acid (D), Methionine (M), Cysteine (C), Phenylalanine (P), Glutamic acid (E), Threonine (T), Glutamine (Q), Tryptophan (W), Glycine (G), Valine (V), Proline (P), Serine (S), Tyrosine (Y), Arginine (R) and Histidine (H), $G_1$ is hydrophobic group that can be cleaved from $X_3$ or $P_1$ by a protease, preferably trypsin;

Preferably, this an optionally substituted alkyl, optionally substituted alkenyl, optionally substituted alkynyl, optionally substituted aryl, optionally substituted heteroaryl group, an alkyl group substituted with an optionally substituted aryl or heteroaryl group, an alkenyl group substituted with an optionally substituted aryl or heteroaryl group or a natural or unnatural amino acid;

Wherein each $X_1$, $X_2$, and $X_3$ is independently a direct bond, —O—, —S—, —C(O)—, —C(O)—N$R_{100}$—, —C(S)—, —C(S)—N$R_{100}$—, —C(O)O—, —N$R_{100}$— and —S(O)$_2$—; wherein $R_{100}$ is hydrogen, alkyl, substituted alkyl, aryl or substituted aryl.

In a preferred embodiment, $F_1$ is FAM.

In a preferred embodiment, $L_1$ is an alkyl or $C_1$-$C_{10}$ alkyl group.

In a preferred embodiment, $P_1$ is a peptide selected from LGK(Ac) or TGGK(Ac)APR (SEQ ID NO: 4), LGKGGAK(Ac) (SEQ ID NO: 5), TSPQPKK(Ac) (SEQ ID NO: 6), SPQPKK(Ac) (SEQ ID NO: 7), PQPKK(Ac) (SEQ ID NO: 8), TSRHK(Ac) (SEQ ID NO: 9), RGK(Ac), LGK(COCF$_3$) or TGGK(COCF$_3$)APR (SEQ ID NO: 10), LGKGGAK(COCF$_3$) (SEQ ID NO: 11), TSPQPKK(COCF$_3$) (SEQ ID NO: 12), SPQPKK(COCF$_3$) (SEQ ID NO: 13), PQPKK(COCF$_3$) (SEQ ID NO: 14), TSRHK(COCF$_3$) (SEQ ID NO: 15), RGK(COCF$_3$), RHKK(Ac) (SEQ ID NO: 16), QPKK(Ac) (SEQ ID NO: 17), RHKK(COCF$_3$) (SEQ ID NO: 18), QPKK(COCF$_3$) (SEQ ID NO: 19), RHKK (SEQ ID NO: 20), QPKK (SEQ ID NO: 21), LGK, TGGKAPR (SEQ ID NO: 22), LGKGGAK (SEQ ID NO: 23), TSPQPKK (SEQ ID NO: 24), SPQPKK (SEQ ID NO: 25), PQPKK (SEQ ID NO: 26), TSRHK (SEQ ID NO: 27) or RGK; more preferably LGK, LGK(Ac) or LGK(COCF$_3$).

In a preferred embodiment, $G_1$ is methyl coumarin or coumarin or N-methyl-3-phenylpropanamide.

In a preferred embodiment, $X_1$ is selected from —O—, —C(O)NH—, —C(O)— and —C(O)O—.

In a preferred embodiment, $X_2$ is selected from —O—, —C(O)NH—, —C(O)— and —C(O)O—.

In a preferred embodiment, $X_3$ is selected from —O—, —C(O)NH—, —C(O)— and —C(O)O—.

In a preferred embodiment, $F_1$ is selected from Table A:

TABLE A

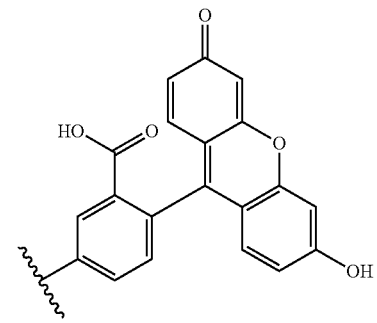 [SMILES: *c1ccc(-c2c3ccc(=O)cc-3oc3cc(O)ccc23)c(C(=O)O)c1]

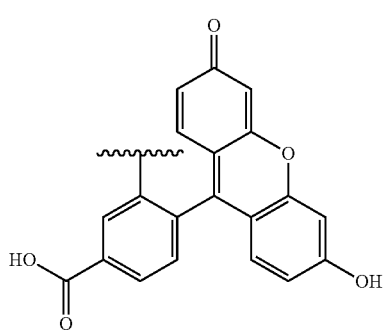 [SMILES: *c1cc(C(=O)O)ccc1-c1c2ccc(=O)cc-2oc2cc(O)ccc12]

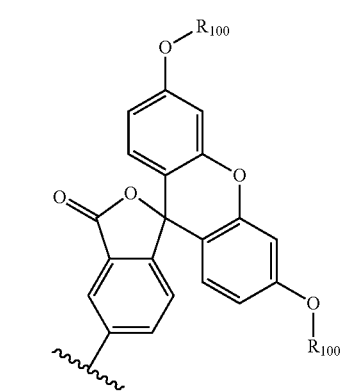

TABLE A-continued

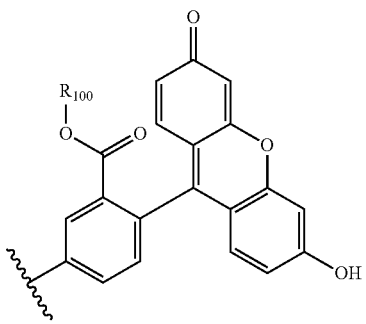

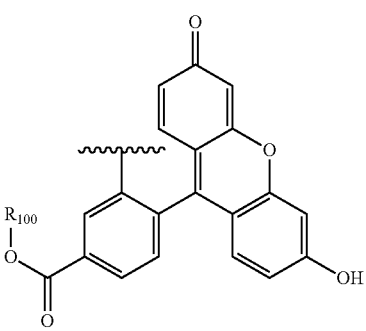

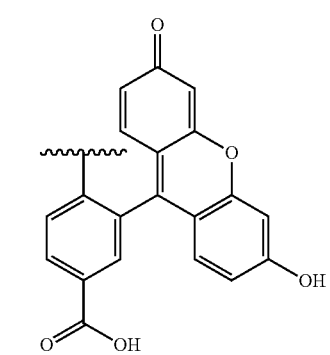

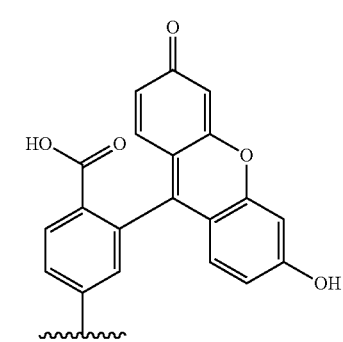

Wherein a is 0, 1, 2, 3, 4, 5, 6, 7, 8, 9 or 10.

In a preferred embodiment, $L_1$ is selected from Table B:

TABLE B

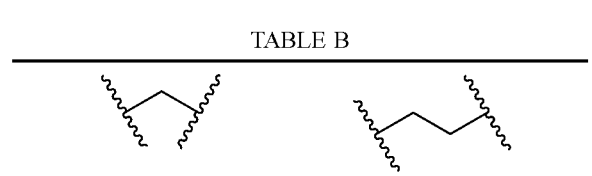

TABLE B-continued

[chemical structures]

Wherein each t is independently 0, 1, 2, 3, 4, 5, 6, 7, 8, 9, 10, 11, 12, 13, 14, 15, 16, 17, 18, 19, 20, 21, 22, 23 or 24;
i is 1, 2, 3, 4, 5 or 6;
j is 0, 1, 2, 3, 4, 5, 6, 7, 8, 9 or 10;
u is an integer between 1 and 500 or between 1 and 10 or between 1 and 20 or between 1 and 100 or between 1 and 300;
Each $R_{101}$ and $R_{102}$ is independently selected from hydrogen, halogen, $-OR_{20}$, $-SR_{20}$, $-NR_{20}R_{21}$, $-CF_3$, $-CN$, $-NO_2$, $-N_3$, $-C(O)OR_{20}$, $-C(O)R_{20}$, $-C(O)NR_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl $-S(O)_2R_{100}$, $-S(O)_3R_{100}$, $-S(O)_3H$,
Alternatively, two $R_{101}$ and $R_{102}$ groups together with the atom or atoms to which they are attached may form one, two or three rings with optional additional substitution.
In a preferred embodiment, $P_1$ is selected from Table C:

TABLE C

[chemical structures]

TABLE C-continued
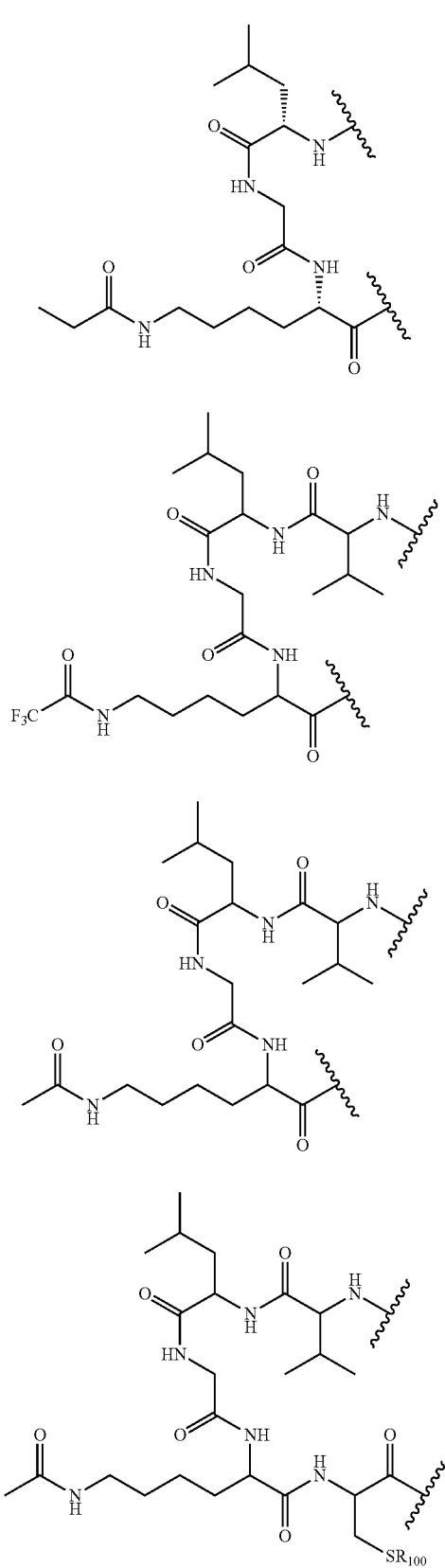
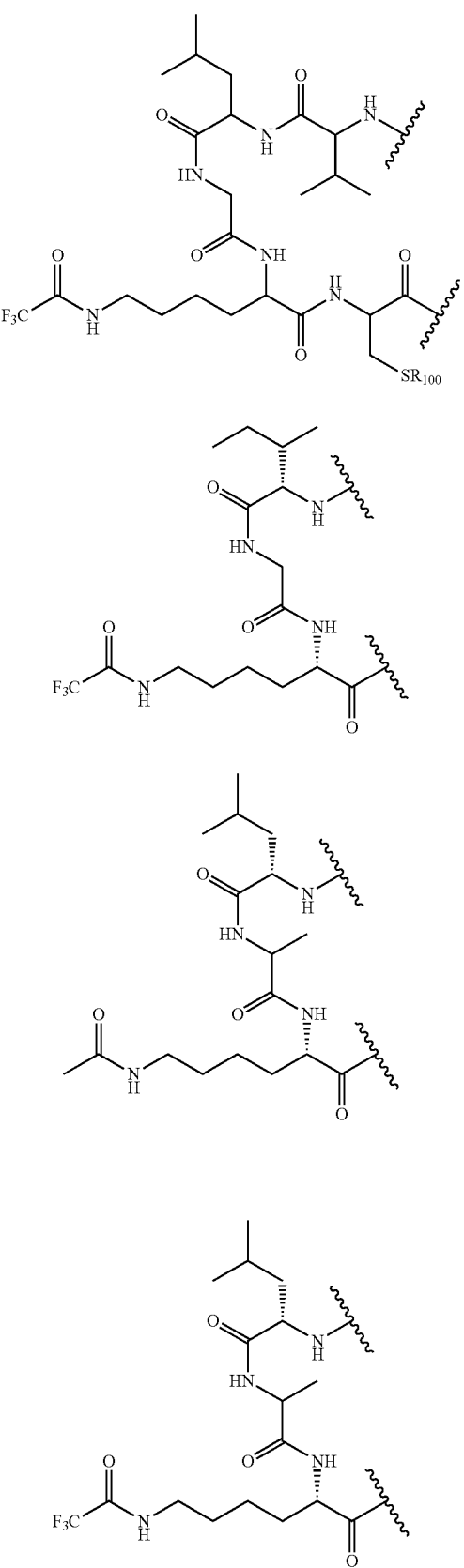

TABLE C-continued
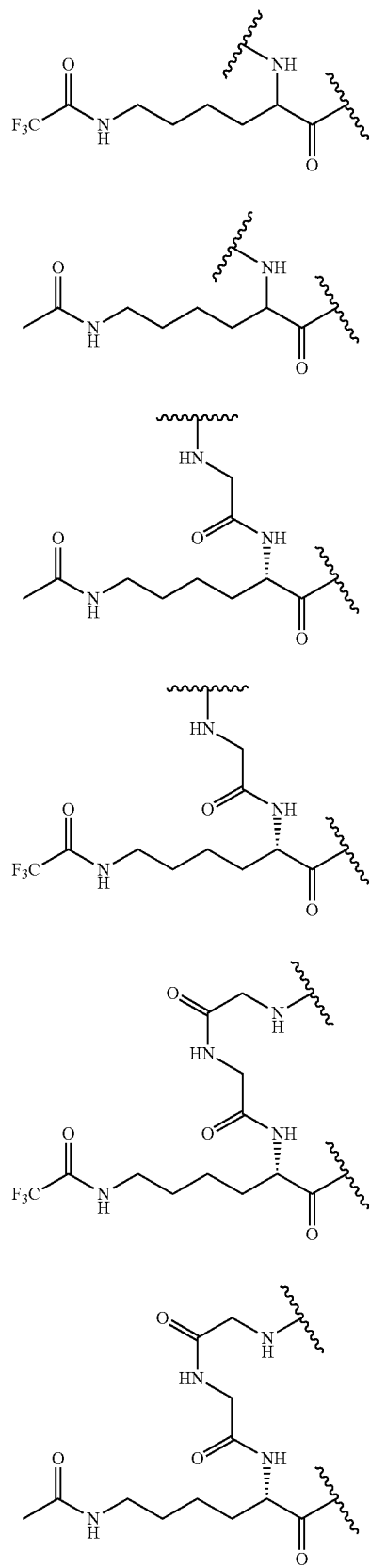
TABLE C-continued
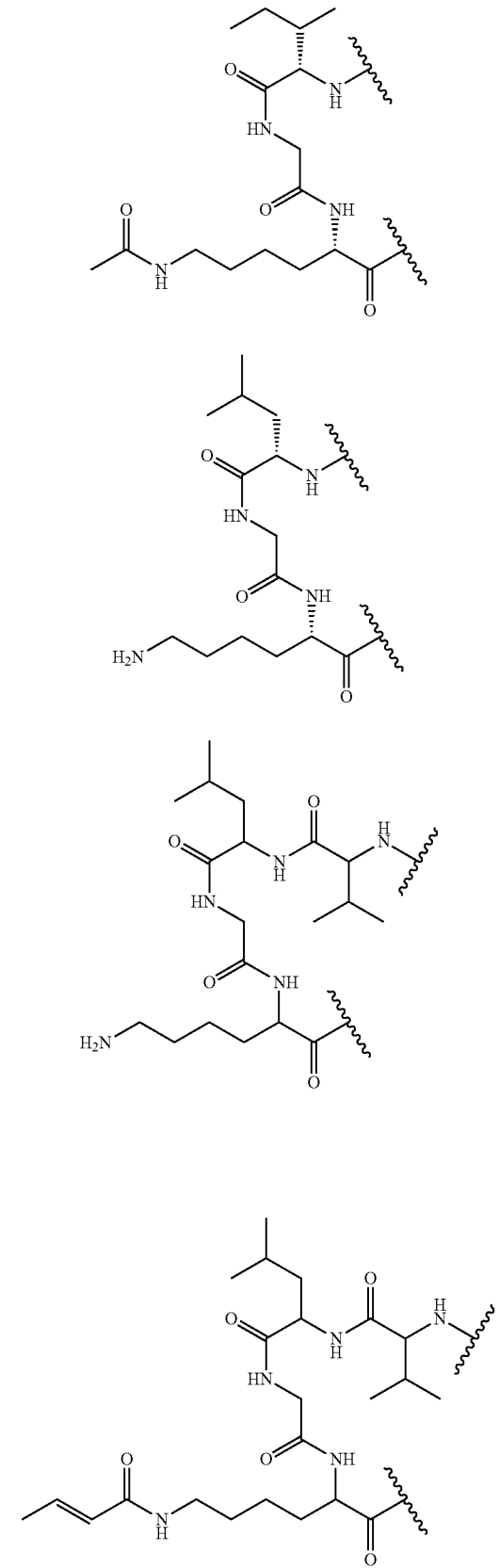

TABLE C-continued
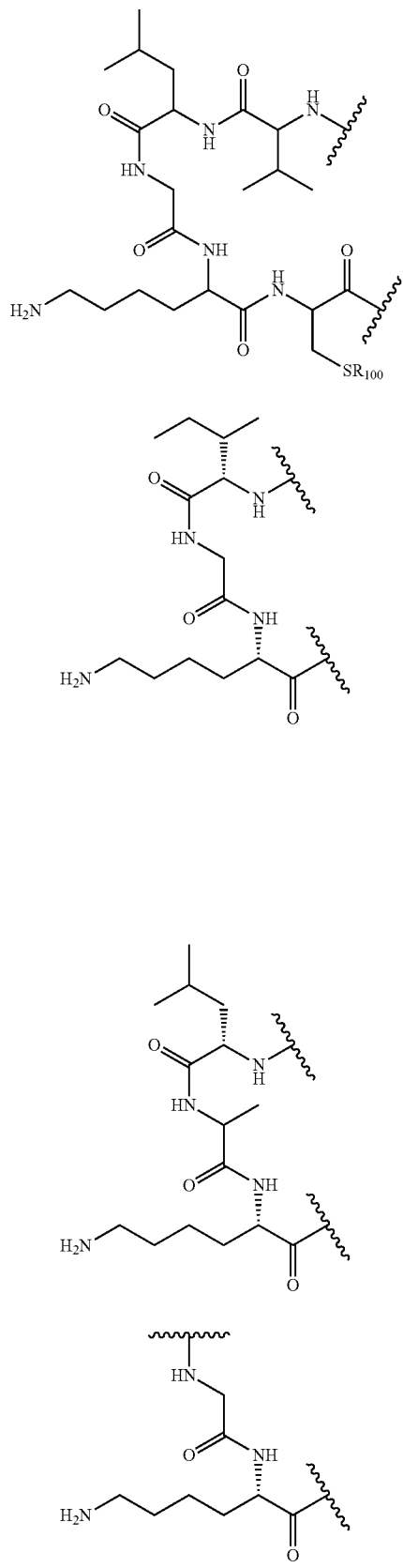
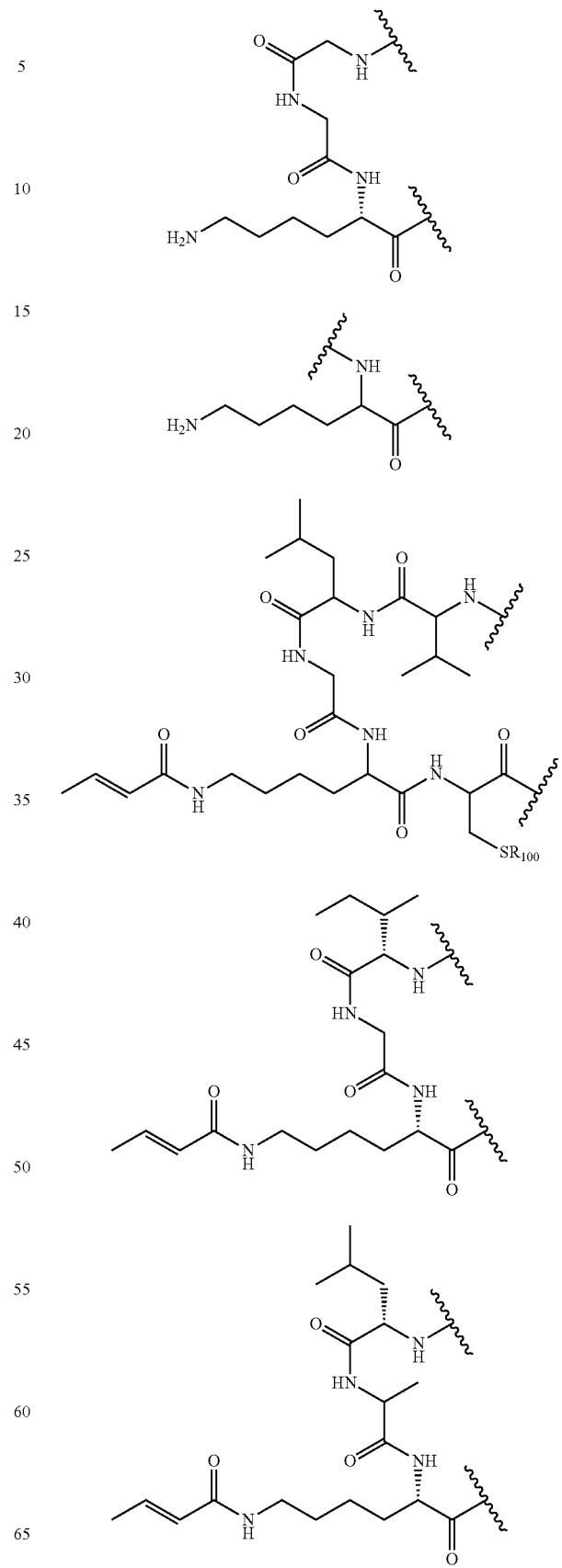

TABLE C-continued
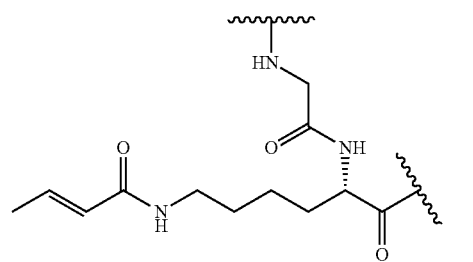 [SMILES: *NCC(=O)N[C@@H](CCCCNC(=O)/C=C/C)C(*)=O]
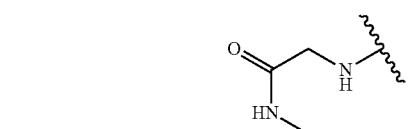
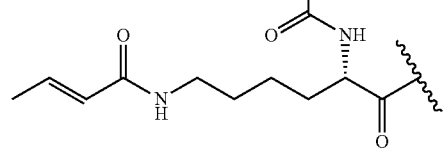
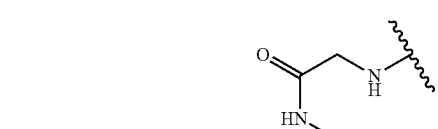
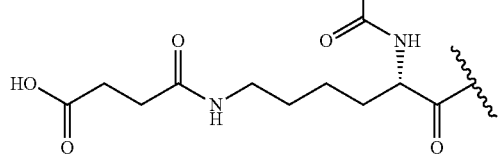
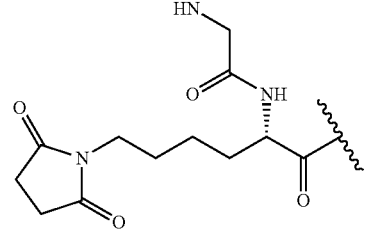
TABLE C-continued
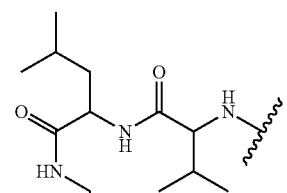
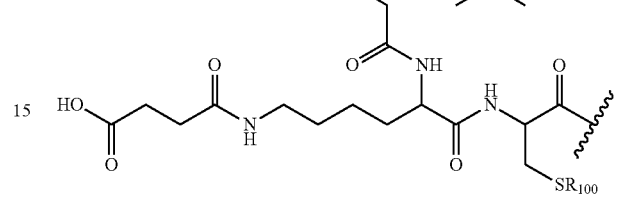
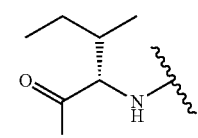
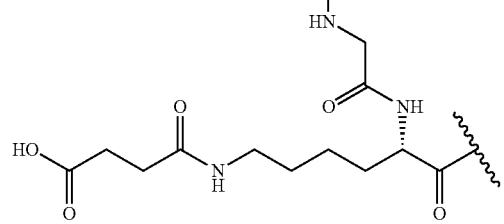
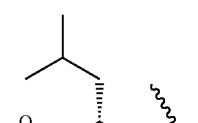
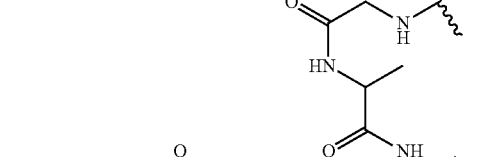
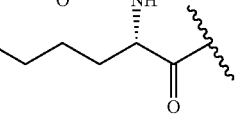
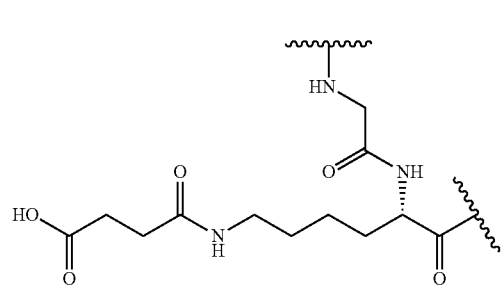 [SMILES: *NCC(=O)N[C@@H](CCCCNC(=O)CCC(=O)O)C(*)=O]

TABLE C-continued
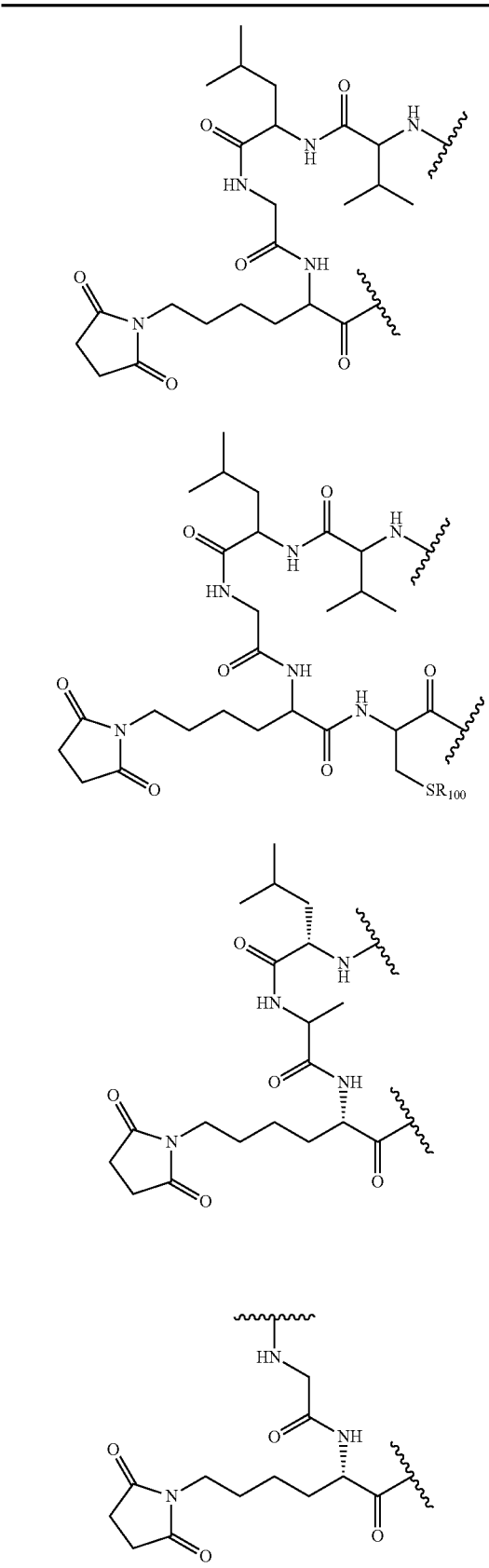
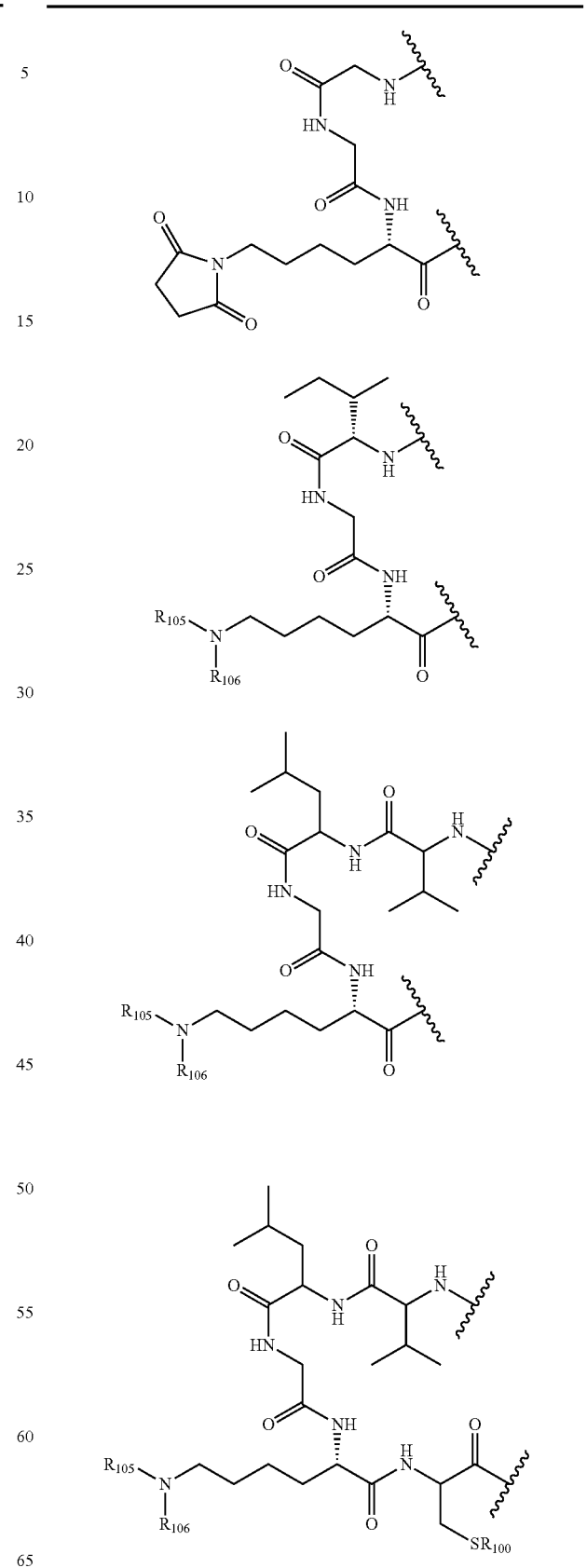

TABLE C-continued
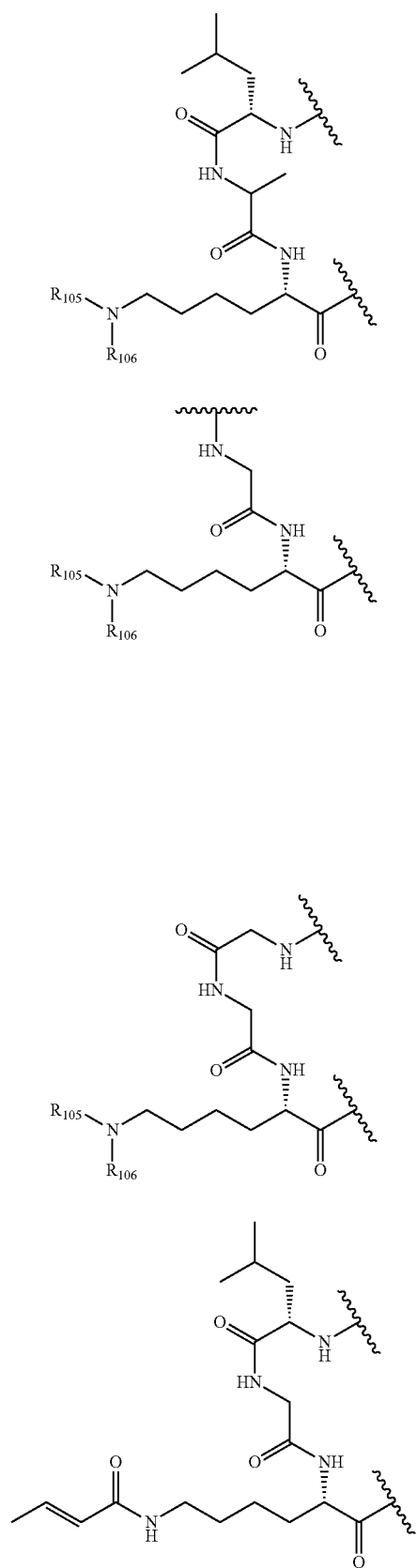
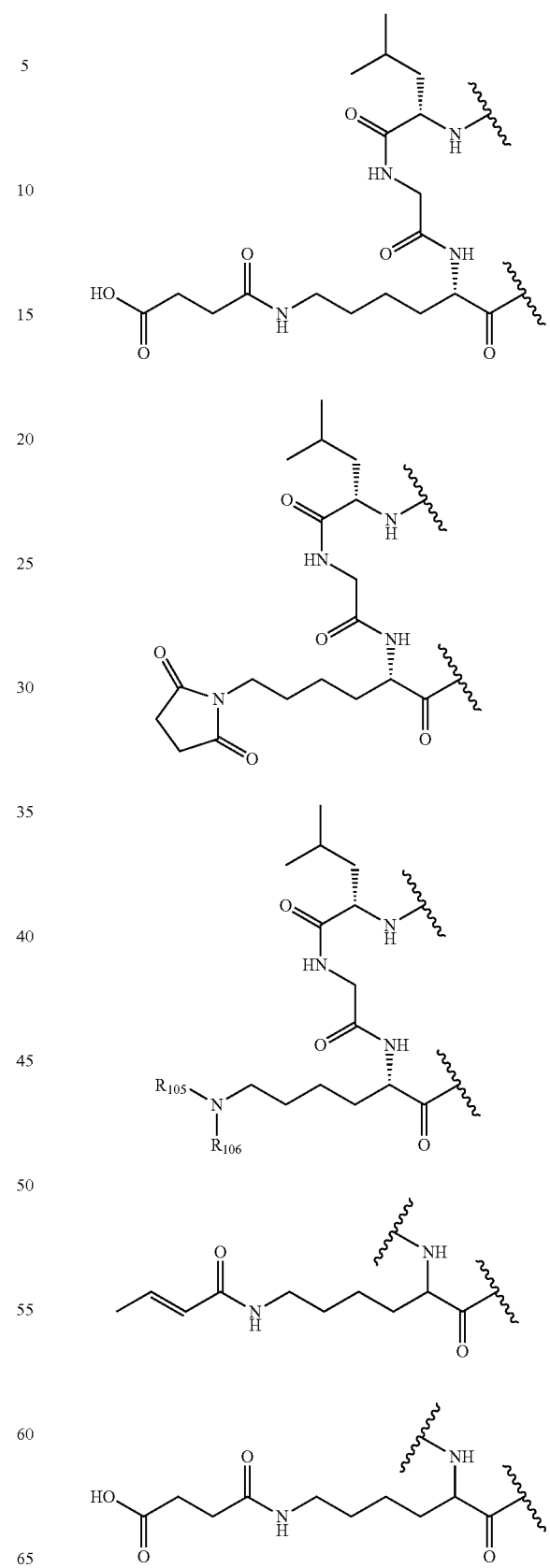

TABLE C-continued
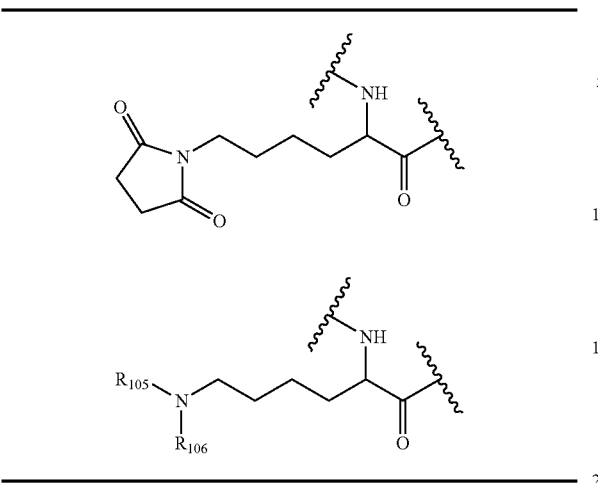
wherein each $R_{105}$ and $R_{106}$ is independently hydrogen, —C(O)alkyl, —C(S)alkyl, —C(O)substituted alkyl, —C(S) substituted alkyl, C(O)aryl, —C(S)aryl, —C(O)substituted aryl, —C(S)substituted aryl, —S(O)alkyl, —S(O)$_2$alkyl, alkyl, substituted alkyl, aryl or substituted aryl.
In a preferred embodiment, $G_1$ is selected from Table D:
TABLE D
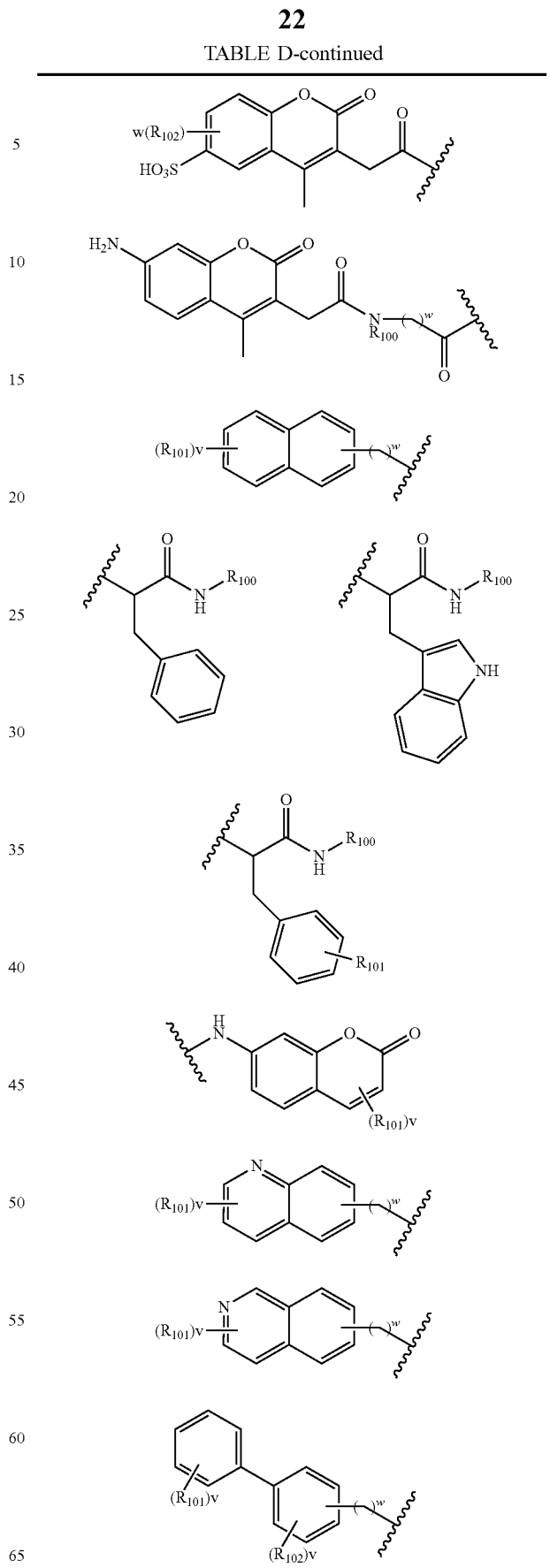

TABLE D-continued
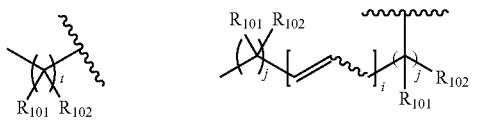
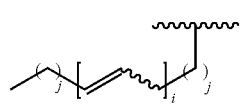
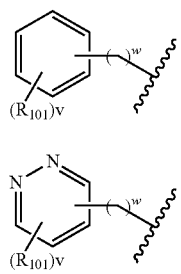
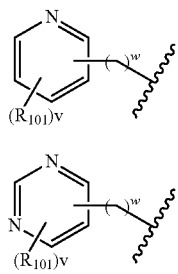
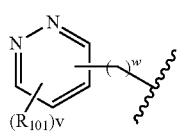
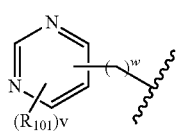
TABLE D-continued
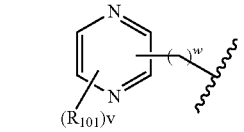
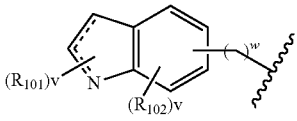
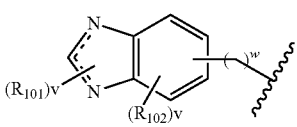
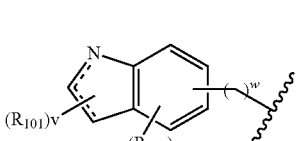
Each v and w is independently 0, 1, 2, 3 or 4;
In a preferred embodiment, the invention relates to the compounds of Table E.
TABLE E
Broad Substrate D
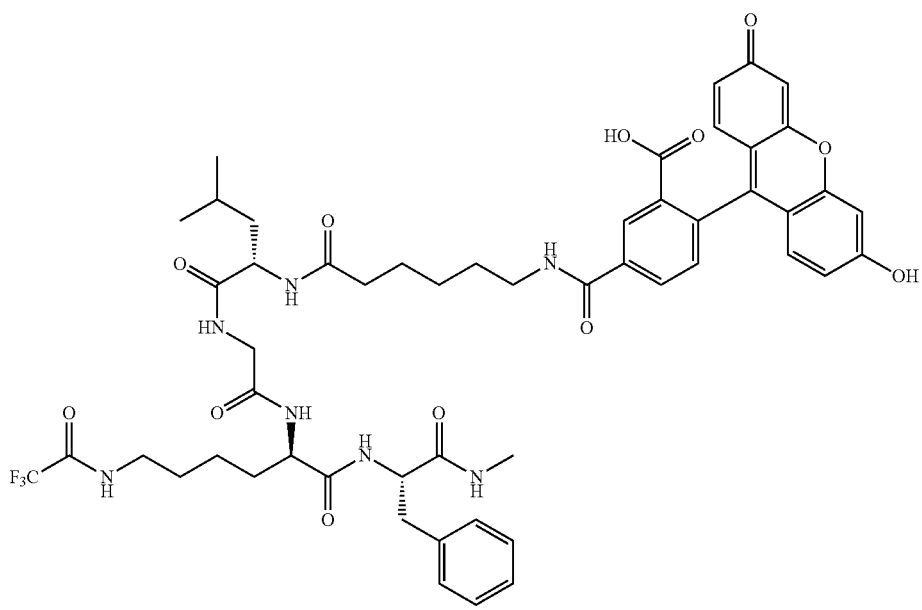 [SMILES: CNC(=O)[C@H](Cc1ccccc1)NC(=O)[C@@H](CCCCNC(=O)C(F)(F)F)NC(=O)CNC(=O)[C@H](CC(C)C)NC(=O)CCCCCNC(=O)c1ccc(-c2c3ccc(=O)cc-3oc3cc(O)ccc23)c(C(=O)O)c1]

TABLE E-continued
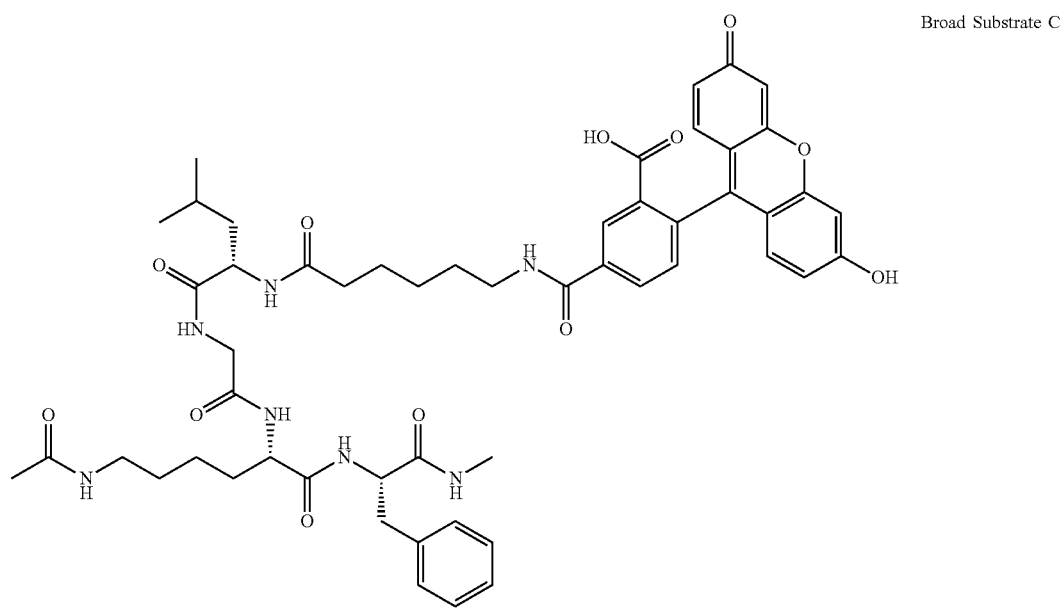
Broad Substrate C
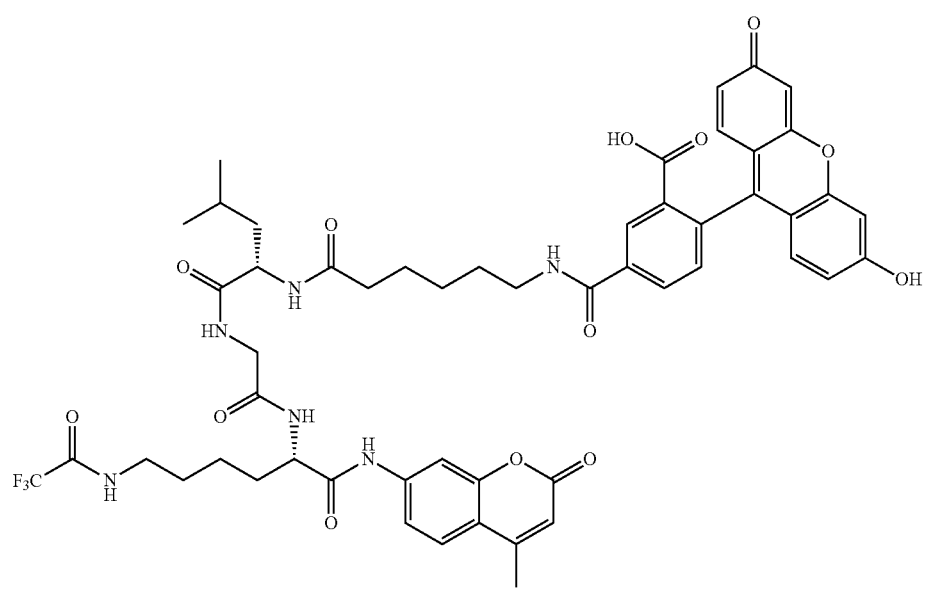 [SMILES: Cc1cc(=O)oc2cc(NC(=O)[C@H](CCCCNC(=O)C(F)(F)F)NC(=O)CNC(=O)[C@H](CC(C)C)NC(=O)CCCCCNC(=O)c3ccc(-c4c5ccc(=O)cc-5oc5cc(O)ccc45)c(C(=O)O)c3)ccc12]
Broad Substrate B

TABLE E-continued

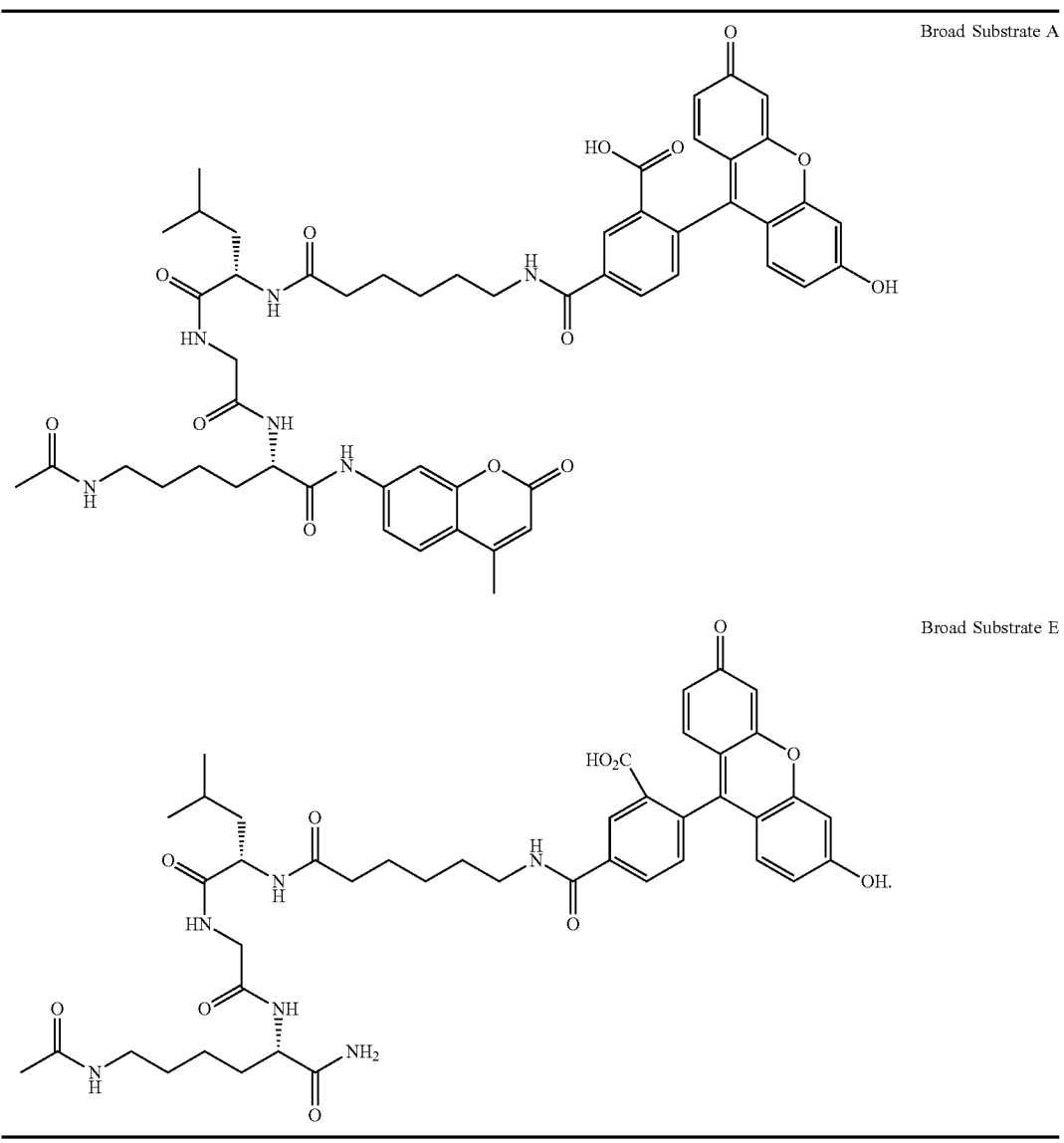

The invention further comprises a method for determining Lysine modifying enzyme activity by incubating the enzyme with a compound of Formula I. In one embodiment, the enzyme activity determination comprise the step of incubating the enzyme with a compound of Formula I (aka the substrate) and monitoring the product formation over time.

In one embodiment, the invention relates to a method for determining an HDAC enzyme activity by incubating an HDAC enzyme with a compound of Formula I wherein the compound of Formula I has a substituted lysine residue, preferably acetyl or trifluoroacetyl substituted lysine residue. In a preferred embodiment, the HDAC enzyme is an isoform selected from HDAC 1, 2, 3, 4, 5, 6, 7, 8, 9, 10, 11 or SIRT 1, 2, 3, 4, 5, 6 or 7. In one embodiment, the HDAC activity determination comprises the step of incubating an HDAC enzyme with a compound of Formula I (aka the substrate) and monitoring the product formation over time by fluorescence wherein the compound of Formula I has a substituted lysine residue, preferably acetyl or trifluoroacetyl substituted lysine residue. In one embodiment, the product is separated from the substrate using a microfluidic mobility shift technology. In one embodiment, the compound of Formula I is incubated with an HDAC enzyme followed by incubation with trypsin wherein trypsin can lead to the cleavage of $G_1$. In one embodiment, the release of G1 is monitored by fluorescence and correlated with HDAC activity.

In one embodiment, the invention relates to a method for evaluating histone acetyltransferase activity comprising the step of incubating histone acetyltransferase enzyme with a compound of Formula I, wherein said compound of Formula I contains an unsubstituted lysine residue, and determining the activity of the histone acetyltransferase enzyme.

The invention further comprises a method for determining an enzyme activity comprising the step of incubating a compound that can be modified by two or more enzymes wherein the first enzyme is lysine modifying and wherein said compound comprises at least one fluorescent moiety and a chromophore moiety wherein one of chromophore moiety can be cleaved by a second enzyme. In a preferred embodiment the substrate is a compound of claim 1 and the chromophore is $G_1$, preferably coumarin. In a preferred embodiment, the fluorescent moiety is Fluorescein based fluorophore, preferably FAM, most preferably 6-FAM. In a preferred embodiment, the chromophore is cleaved following the treatment with trypsin.

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g., single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g., pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g., morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g., benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The term natural amino acid includes the following naturally occurring amino acids: Isoleucine, Alanine, Leucine, Asparagine, Lysine, Aspartic acid, Methionine, Cysteine, Phenylalanine, Glutamic acid, Threonine, Glutamine, Tryptophan, Glycine, Valine. Proline, Selenocysteine, Serine, Tyrosine, Arginine, Histidine, Ornithine and Taurine. As used herein the modified lysine residues K(Ac) and K(COCF$_3$), as part of a peptide or conjugate has the following structures:

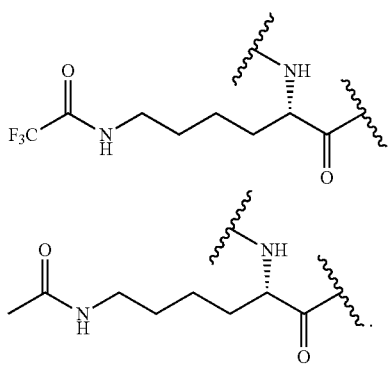

The terms "compound" "drug", and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

EXAMPLES

Example 1: Synthesis of 5-(((4S,7S,13S)-4-benzyl-13-isobutyl-3,6,9,12,15-pentaoxo-7-(4-(2,2,2-trifluoroacetamido)butyl)-2,5,8,11,14-pentaazaicosan-20-yl)carbamoyl)-2-(6-hydroxy-3-oxo-3H-xanthen-9-yl) benzoic Acid, Broad Substrate D The compound depicted above was synthesized according to the following procedure:

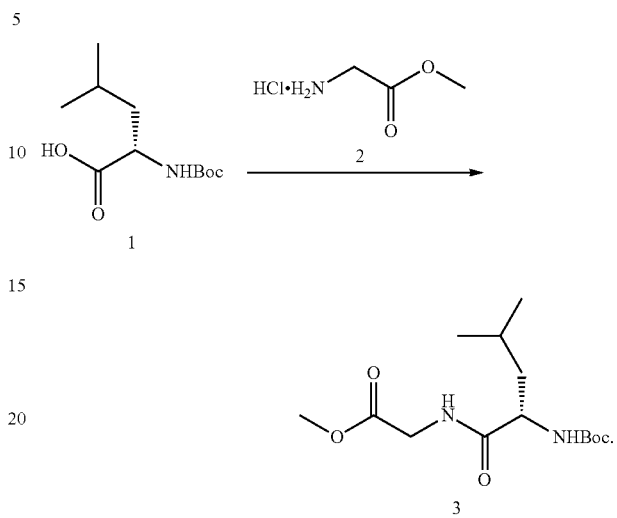

To a solution of (S)-2-((tert-butoxycarbonyl)amino)-4-methylpentanoic acid (1) (10 g, 43.2 mmol, 1.0 equiv.) in THF (90 mL) was added methyl 2-aminoacetate hydrochloride (2) (3.2 g, 43.2 mmol, 1.0 equiv.), Et$_3$N (12.5 g, 124 mmol, 2.9 equiv.) and HATU (16.4 g, 43.2 mmol, 1.0 equiv.). The mixture was stirred at room temperature for 16 h. The reaction was filtered through Celite. The reaction filtrate was diluted with 100 mL of water and stirred for 15 min. The suspension was filtered off, rinsed with water and dried to afford (S)-methyl 2-(2-((tert-butoxycarbonyl)amino)-4-methylpentanamido)acetate (3) (12 g, 92% yield).

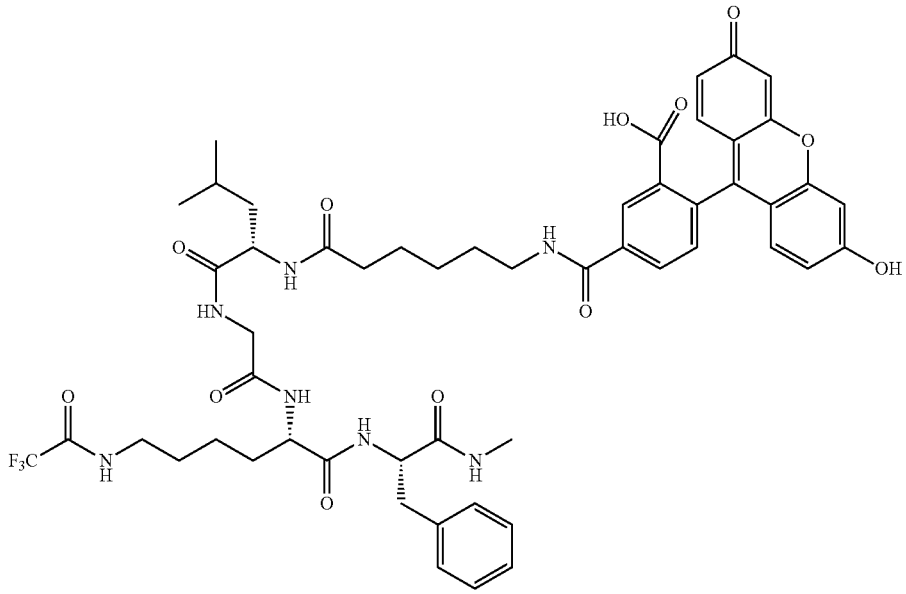 [SMILES: CNC(=O)[C@H](Cc1ccccc1)NC(=O)[C@H](CCCCNC(=O)C(F)(F)F)NC(=O)CNC(=O)[C@H](CC(C)C)NC(=O)CCCCCNC(=O)c1ccc(-c2c3ccc(=O)cc-3oc3cc(O)ccc23)c(C(=O)O)c1]

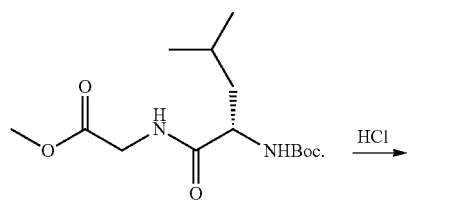

3

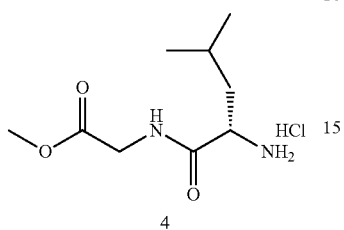

4

To a solution of (S)-methyl 2-(2-((tert-butoxycarbonyl)amino)-4-methylpentanamido) acetate (3) (10 g, 33.1 mmol) in 1,4-dioxane (50 mL) was added a 5M solution of HCl in 1,4-dioxane (50 mL) at room temperature. The reaction was stirred at room temperature for 16 h. The reaction mixture was filtered to afford (S)-methyl 2-(2-amino-4-methylpentanamido)acetate hydrochloride (4) as the filtered solid (7.9 g, 100%).

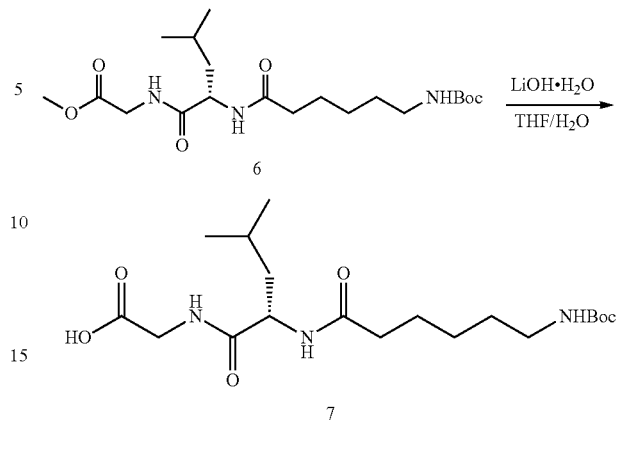

To a solution of (5)-methyl 13-isobutyl-2,2-dimethyl-4,11,14-trioxo-3-oxa-5,12,15-triazaheptadecan-17-oate (6) (5 g, 12 mmol) in THF (50 mL) was added a solution of LiOH.H₂O (1.25 g, 30 mmol, 2.5 equiv.) in water (50 mL) at room temperature. After 3 h, the reaction mixture was concentrated, diluted with water and acidified with a 1N aqueous solution of HCl to about pH4-5. The mixture was stirred for 15 min and the white precipitate formed was filtered off, rinsed with water, and dried to afford (S)-13-isobutyl-2,2-dimethyl-4,11,14-trioxo-3-oxa-5,12,15-triazaheptadecan-17-oic acid (7) (2 g, 42% yield).

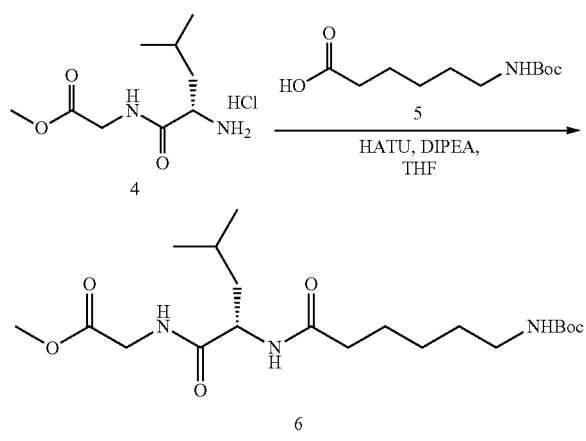

To a solution of (S)-methyl 2-(2-amino-4-methylpentanamido)acetate hydrochloride (4) (5 g, 21 mmol, 1.0 equiv.) in THF (80 mL) was added 6-((tert-butoxycarbonyl)amino) hexanoic acid (4.8 g, 21 mmol, 1.0 equiv.), HATU (12 g, 31.5 mmol, 1.5 equiv.) and DIPEA (10.74 g, 83.2 mmol, 4.0 equiv.). The reaction was stirred at room temperature for 18 h. The mixture was then filtered through Celite. The filtrate was concentrated under reduced pressure and the crude residue was purified by column chromatography (silica gel, CH₂Cl₂/MeOH=50/1) to give (S)-methyl 13-isobutyl-2,2-dimethyl-4,11,14-trioxo-3-oxa-5,12,15-triazaheptadecan-17-oate (6) as a white solid (5 g, 57% yield).

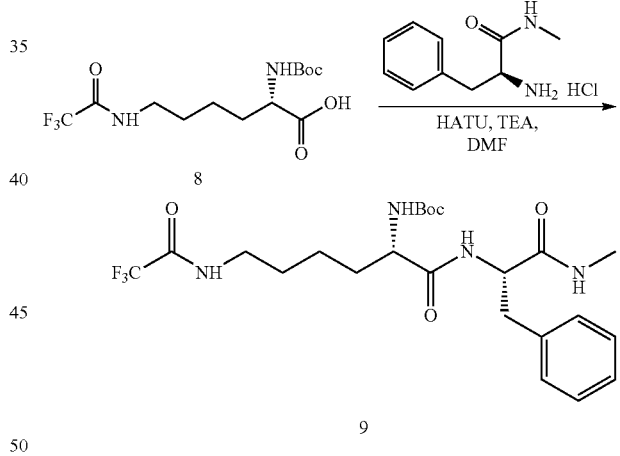

To a solution of (S)-2-((tert-butoxycarbonyl)amino)-6-(2,2,2-trifluoroacetamido)hexanoic acid (8) (0.90 g, 2.63 mmol, 1.0 equiv.) in DMF (25 mL) at room temperature was added (S)-2-amino-N-methyl-3-phenylpropanamide hydrochloride (0.56 g, 2.63 mmol, 1.0 equiv.), HATU (3.99 g, 10.51 mmol, 4.0 equiv.) and triethylamine (2.13 g, 21.02 mmol, 8.0 equiv.). The reaction was stirred at room temperature for 2 h. A saturated solution of sodium bicarbonate was added. The product was extracted with ethyl acetate. The combined organic layers were washed with water, dried over sodium sulfate, filtered and concentrated under reduced pressure. The crude residue was purified by prep-HPLC to afford tert-butyl ((S)-1-(((S)-1-(methylamino)-1-oxo-3-phenylpropan-2-yl)amino)-1-oxo-6-(2,2,2-trifluoroacetamido)hexan-2-yl)carbamate (9) (0.86 g, 65% yield) as a solid.

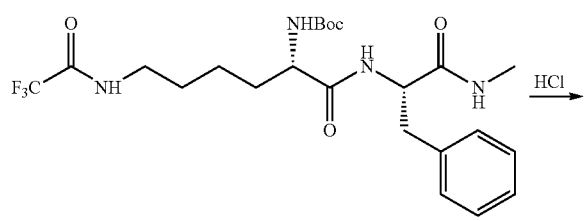

9

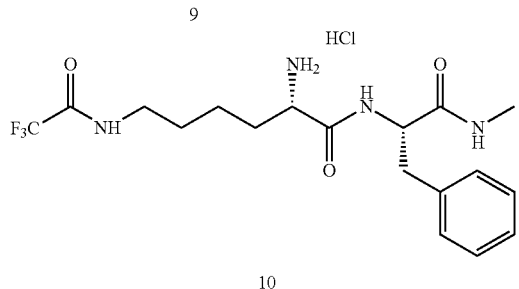

10

To a solution of tert-butyl ((S)-1-(((S)-1-(methylamino)-1-oxo-3-phenylpropan-2-yl)amino)-1-oxo-6-(2,2,2-trifluoroacetamido)hexan-2-yl)carbamate (9) (0.38 g, 0.87 mmol) in 1,4-dioxane (10 mL) was added a 5M solution of HCl in 1,4-dioxane (20 mL). The reaction was stirred at room temperature for 3 h. The mixture was concentrated under reduced pressure to afford (S)-2-amino-N—((S)-1-(methylamino)-1-oxo-3-phenylpropan-2-yl)-6-(2,2,2-trifluoroacetamido)hexanamide hydrochloride (10) (0.33 g, 100% yield).

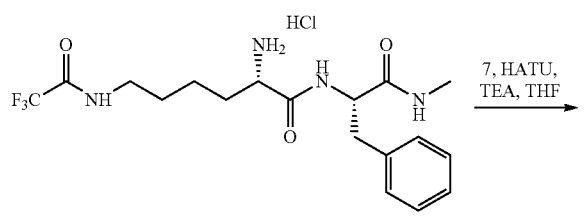

10

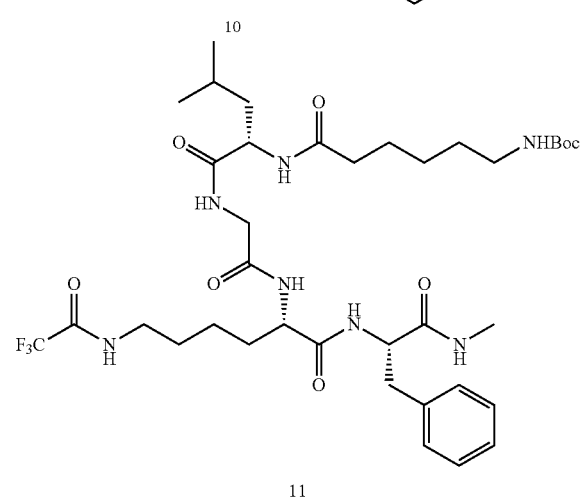

11

To a solution of (S)-2-amino-N—((S)-1-(methylamino)-1-oxo-3-phenylpropan-2-yl)-6-(2,2,2-trifluoroacetamido)hexanamide hydrochloride (10) (0.33 g, 0.82 mmol) in THF (20 mL) were added 7 (0.36 g, 0.82 mmol, 1.0 equiv.), HATU (0.68 g, 1.65 mmol, 2.0 equiv.) and triethylamine (0.54 g, 4.94 mmol, 6.0 equiv.). The reaction was stirred at room temperature for 3 h. A saturated solution of sodium bicarbonate was added. The product was extracted with ethyl acetate. The combined organic layers were washed with water, dried avec sodium sulfate, filtered and concentrated under reduced pressure. The crude material was purified by silica gel column (prep-HPLC) to afford tert-butyl ((4S,7S,13S)-4-benzyl-13-isobutyl-3,6,9,12,15-pentaoxo-7-(4-(2,2,2-trifluoroacetamido) butyl)-2,5,8,11,14-pentaazaicosan-20-yl)carbamate (11) (0.35 g, 51% yield).

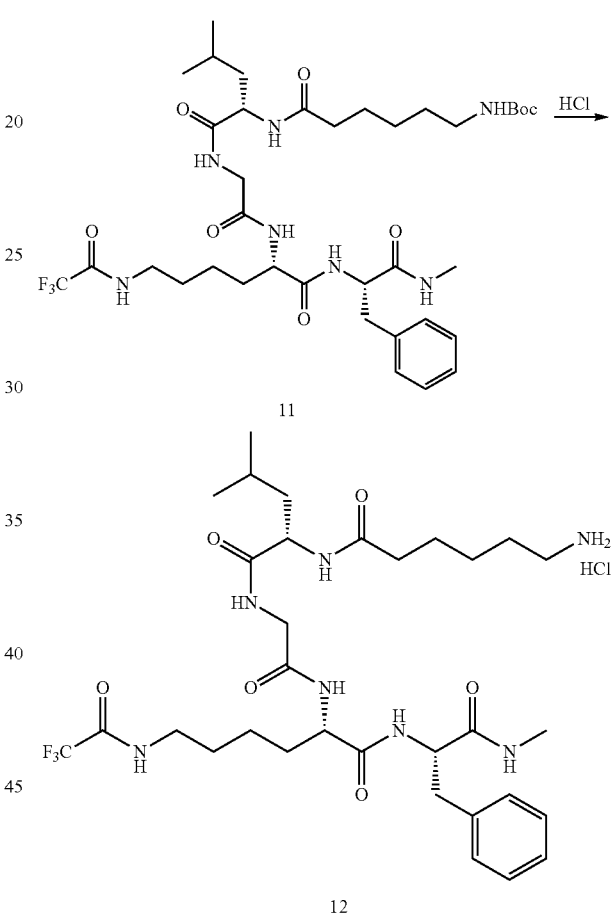

11

12

To a solution of tert-butyl ((4S,7S,13S)-4-benzyl-13-isobutyl-3,6,9,12,15-pentaoxo-7-(4-(2,2,2-trifluoroacetamido) butyl)-2,5,8,11,14-pentaazaicosan-20-yl)carbamate (11) (0.38 g, 0.87 mmol) in 1,4-dioxane (10 mL) and was added a 5M solution of HCl in 1,4-dioxane (20 mL). The reaction was stirred at room temperature for 3 h. The reaction was then concentrated and dried under reduced pressure to afford (S)-2-(2-((S)-2-(6-aminohexanamido)-4-methylpentanamido)acetamido)-N—((S)-1-(methylamino)-1-oxo-3-phenylpropan-2-yl)-6-(2,2,2-trifluoroacetamido)hexanamide (12) (0.33 g, 100% yield).

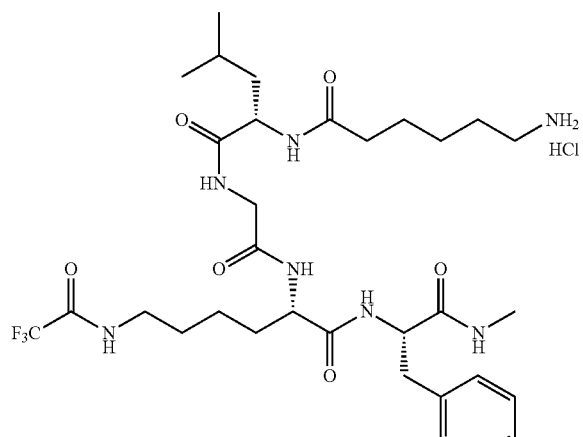
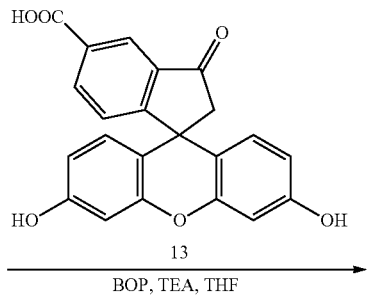

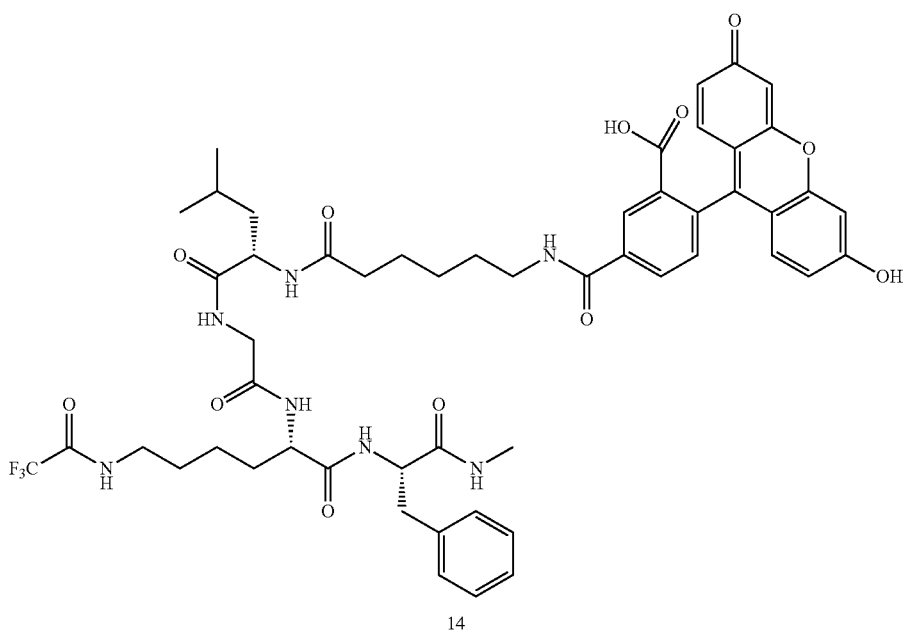

To a solution of (S)-2-(2-((S)-2-(6-aminohexanamido)-4-methylpentanamido)acetamido)-N—((S)-1-(methylamino)-1-oxo-3-phenylpropan-2-yl)-6-(2,2,2-trifluoroacetamido)hexanamide (12) (0.22 g, 0.32 mmol, 1.0 equiv.) in THF (10 mL) at room temperature was added 5-FAM (13) (0.11 g, 0.32 mmol, 1.0 equiv.), BOP (0.44 g, 1.0 mmol, 3.1 equiv.) and triethylamine (0.6 mL). The reaction was stirred at room temperature for 22 h. The mixture was then filtered through Celite. The filtrate was concentrated under reduced pressure. The crude residue was purified by prep-HPLC to give 5-(4S,7S,13S)-4-benzyl-13-isobutyl-3,6,9,12,15-pentaoxo-7-(4-(2,2,2-trifluoroacetamido)butyl)-2,5,8,11,14-pentaaza-icosan-20-yl)carbamoyl)-2-(6-hydroxy-3-oxo-3H-xanthen-9-yl)benzoic acid (14) as a yellow solid (13 mg, 3.9% yield). ESI+ MS: m/z 1044 ([M+H]$^+$), 1H NMR (MeOD, 500 Hz) δ 0.92 (d, J=6.5 Hz, 3H), 0.97 (d, J=6.5 Hz, 3H), 1.16-1.19 (m, 2H), 1.27-1.31 (m, 2H), 1.45-1.48 (m, 4H), 1.61-1.71 (m, 8H), 2.31-2.33 (m, 2H), 2.70 (s, 3H), 2.81-2.84 (m, 1H), 2.96-2.98 (m, 1H), 3.17-3.19 (m, 3H), 3.44 (t, J=9.0 Hz, 2H), 3.75 (d, J=15.5 Hz, 1H), 3.92 (d, J=15.5 Hz, 1H), 4.12-4.14 (m, 1H), 4.28-4.30 (m, 1H), 4.50-4.52 (m, 1H), 6.52-6.54 (m, 2H), 6.58 (d, J=8.5 Hz, 2H), 6.68 (d, J=1.5 Hz, 2H), 7.18-7.29 (m, 6H), 8.18 (d, J=8 Hz, 1H), 8.42 (s, 1H).

Example 2: Synthesis of 5-(((4S,7S,13S)-7-(4-acetamidobutyl)-4-benzyl-13-isobutyl-3,6,9,12,15-pentaoxo-2,5,8,11,14-pentaazaicosan-20-yl)carbamoyl)-2-(6-hydroxy-3-oxo-3H-xanthen-9-yl)benzoic Acid, Broad Substrate C

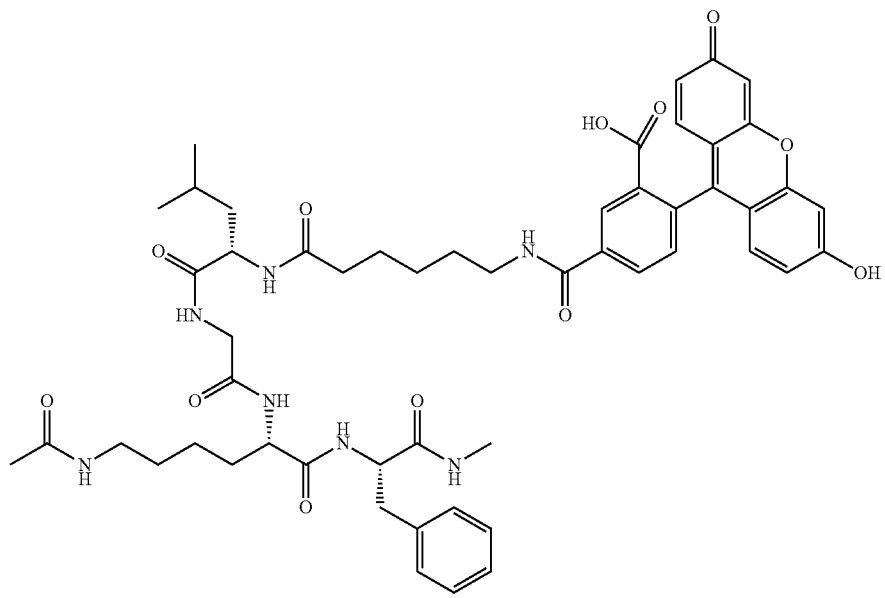 [SMILES: CNC(=O)[C@H](Cc1ccccc1)NC(=O)[C@H](CCCCNC(C)=O)NC(=O)CNC(=O)[C@H](CC(C)C)NC(=O)CCCCCNC(=O)c1ccc(-c2c3ccc(=O)cc-3oc3cc(O)ccc23)c(C(=O)O)c1]

The above depicted compound was synthesized using a similar procedure as Example 1. ESI+MS: m/z 990 ([M+H]$^+$).

Example 3: 2-(6-hydroxy-3-oxo-3H-xanthen-9-yl)-5-(((8S,14S)-1,1,1-trifluoro-14-isobutyl-8-((4-methyl-2-oxo-2H-chromen-7-yl)carbamoyl)-2,10,13,16-tetraoxo-3,9,12,15-tetraazahenicosan-21-yl)carbamoyl)benzoic Acid, Broad Substrate B

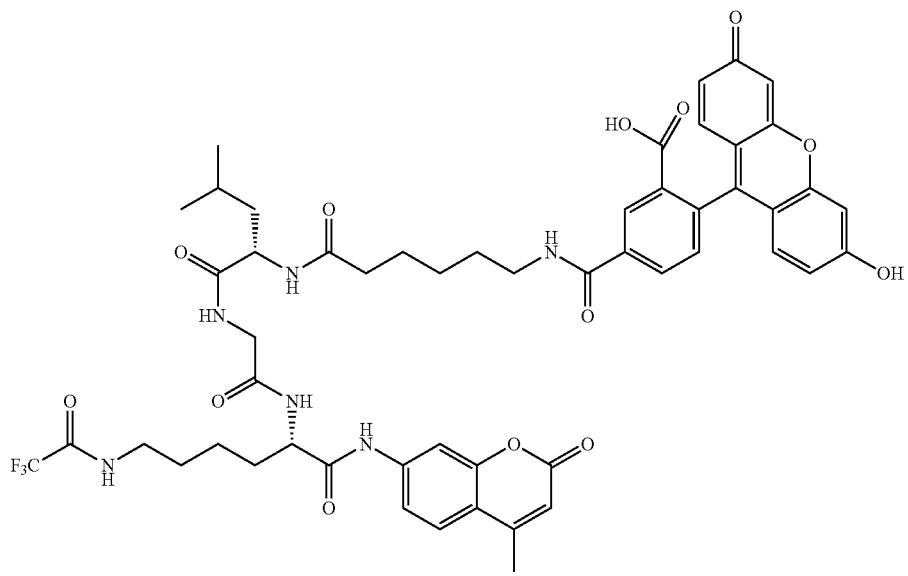 [SMILES: Cc1cc(=O)oc2cc(NC(=O)[C@H](CCCCNC(=O)C(F)(F)F)NC(=O)CNC(=O)[C@H](CC(C)C)NC(=O)CCCCCNC(=O)c3ccc(-c4c5ccc(=O)cc-5oc5cc(O)ccc45)c(C(=O)O)c3)ccc12]

The above depicted compound was synthesized using a similar procedure as Example 1. ESI+MS: m/z 1041 ([M+H]$^+$).

Example 4: 2-(6-hydroxy-3-oxo-3H-xanthen-9-yl)-5-(((8S,14S)-14-isobutyl-8-((4-methyl-2-oxo-2H-chromen-7-yl)carbamoyl)-2,10,13,16-tetraoxo-3,9,12,15-tetraazahenicosan-21-yl)carbamoyl)benzoic Acid, Broad Substrate A

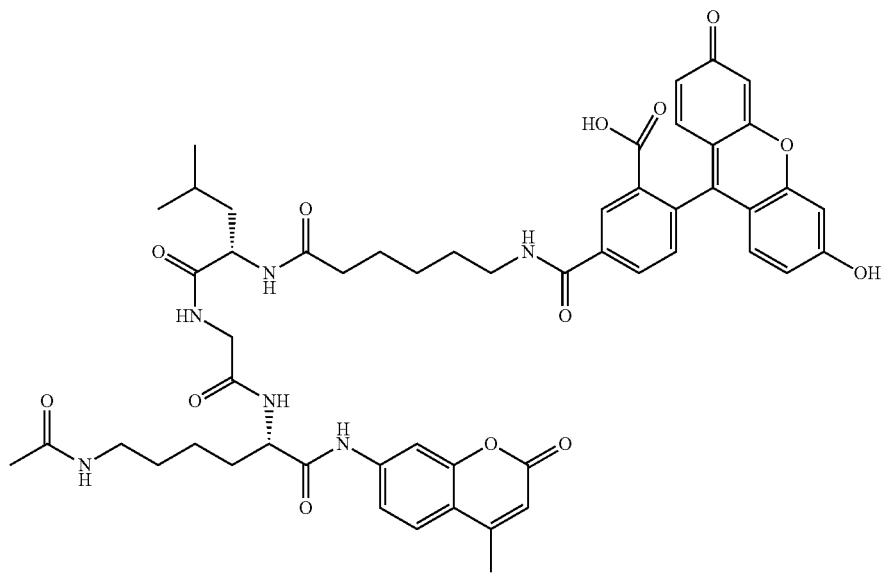 [SMILES: CC(=O)NCCCC[C@H](NC(=O)CNC(=O)[C@H](CC(C)C)NC(=O)CCCCCNC(=O)c1ccc(-c2c3ccc(=O)cc-3oc3cc(O)ccc23)c(C(=O)O)c1)C(=O)Nc1ccc2c(C)cc(=O)oc2c1]

The above depicted compound was synthesized using a similar procedure as Example 1. ESI+MS: m/z 1010 ([M+Na]$^+$).

Example 5: Determination of HDAC Activity and Inhibitory Activity of Reference Compounds Using Compounds of Formula I Materials and Instrument All HDACs were purchased from BPS Bioscience. HDAC substrate H218 was from Caliper Co. and Peptides Broad Substrate A, Broad Substrate E, Broad Substrate B were synthesized in house. The other reagents purchased from Sigma. Caliper EZ reader II system was used to collect all the data.

To test HDAC enzymatic activity, purified HDACs were incubated with 2 μM carboxyfluorescein (FAM)-labeled acetylated peptide substrate for various time at room temperature, in HDAC assay buffer that contained 50 mM HEPES (pH 7.4), 100 mM KCl, 0.01% BSA and 0.001% Tween-20. Reactions were terminated by the addition of the known HDAC inhibitor LBH -589 (panobinostat) with a final concentration of 1.5 μM. Substrate and product were separated electrophoretically and fluorescence intensity in the substrate and product peaks was determined and analyzed by Labchip EZ Reader II. The percentage of substrate conversion was used for HDAC activity comparison.

To test inhibitory activity of reference compounds to HDACs, purified HDACs were incubated with 2 μM carboxyfluorescein (FAM)-labeled acetylated peptide substrate and tested compound at varying doses for one hour at room temperature, in HDAC assay buffer. Reactions were terminated by the addition of the known HDAC inhibitor LBH -589 (panobinostat) with a final concentration of 1.5 μM. The percent inhibition was plotted against the compound concentration and the IC50 value was determined from the logistic dose-response curve fitting by Origin 8.0 software. (Madan Katragadda, Paola Magotti, Ga. Sfyroera, and John D. Lambris, *J. Med. Chem.* 2006, 49, 4616-4622). The reactions were performed in duplicate for each sample.

Example 6: Kinetics of the Inhibition of HDAC 1 with its Inhibitors

Figure 6A:
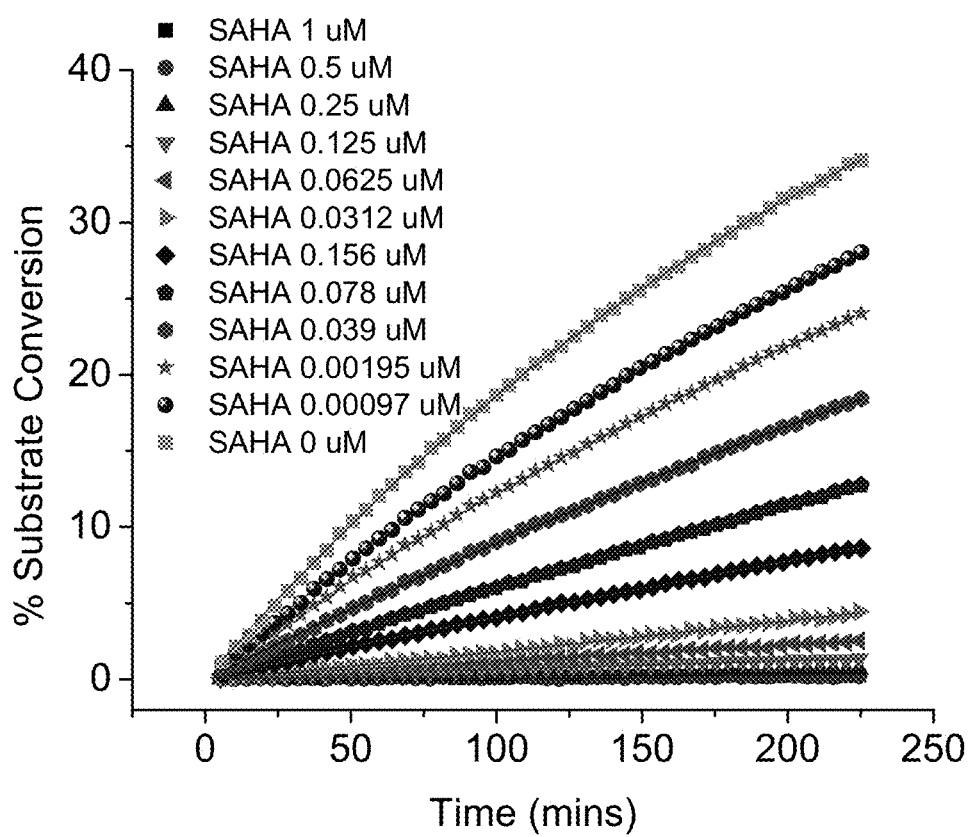
FIG. 6A is a graph which shows a time course of substrate conversion (%) with HDAC 1 in the presence of various concentrations of SAHA (Example 6).
Figure 6B:
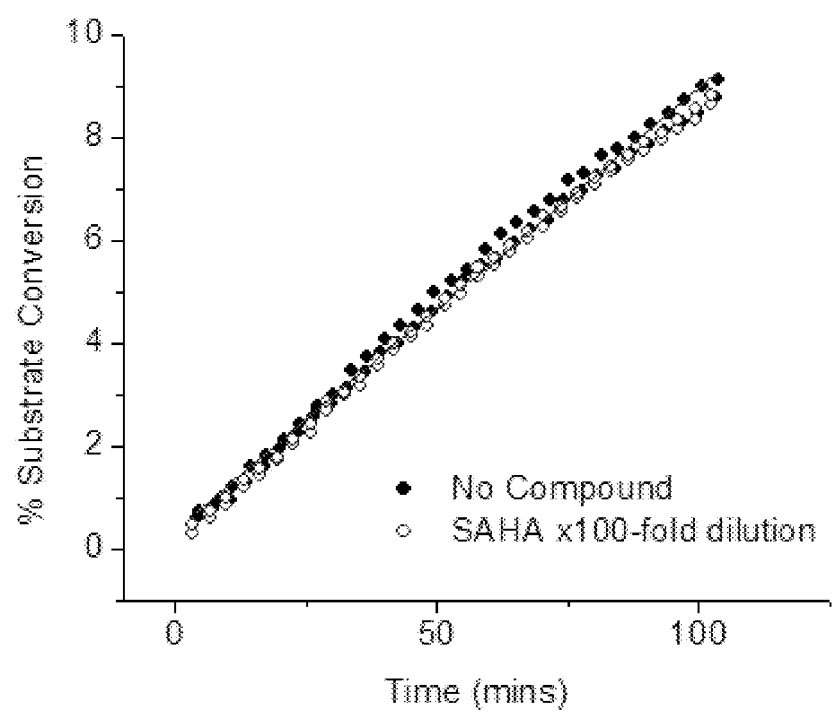
FIG. 6B is a graph which shows substrate conversion (%) over time in a reversibility assay for SAHA (Example 6). The red circles represent compound dilution.
Figure 7A:
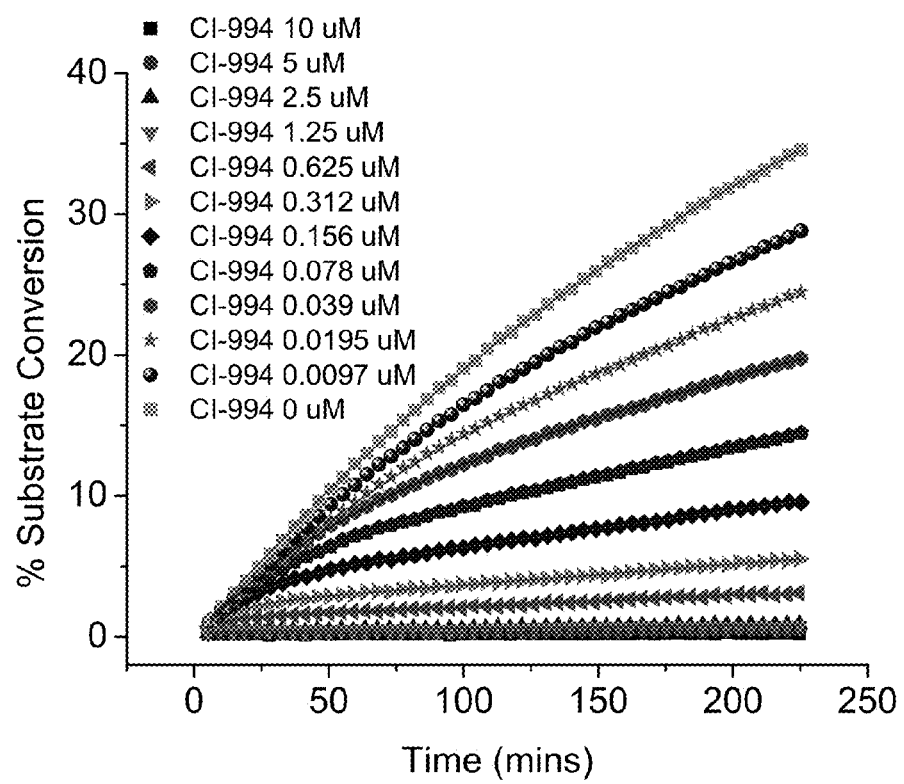
FIG. 7A is a graph which shows a time course of substrate conversion (%) with HDAC 1 in the presence of various concentrations of CI-994 (Example 6).
Figure 7B:
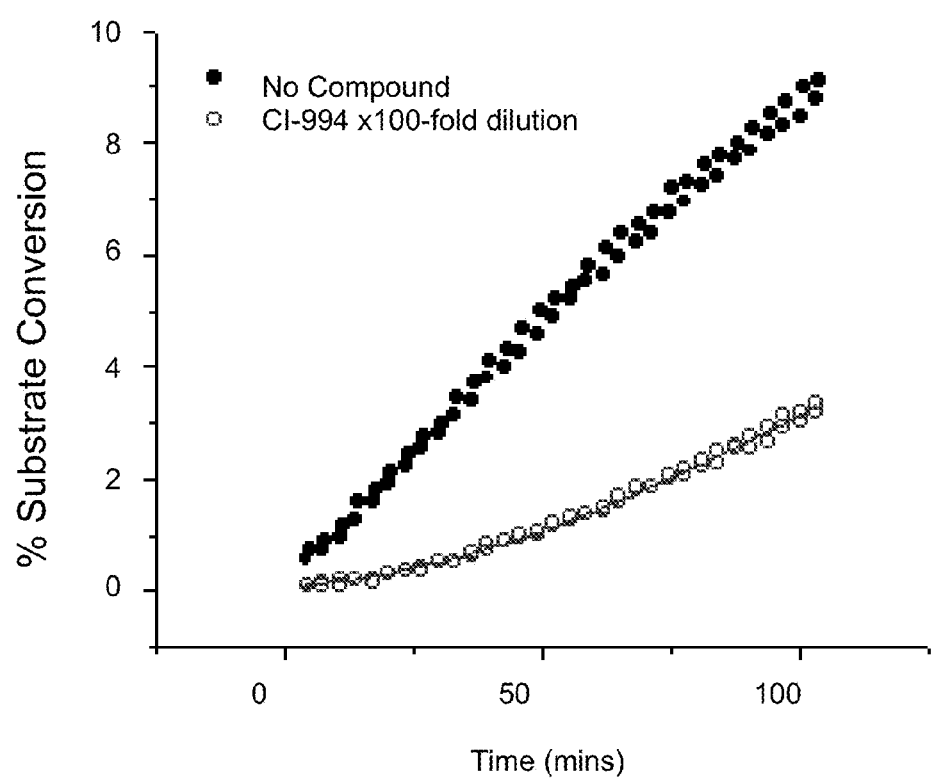
FIG. 7B is a graph which shows substrate conversion (%) over time in a reversibility assay for CI-994(Example 6). The red circles represent compound dilution.
Figure 8:
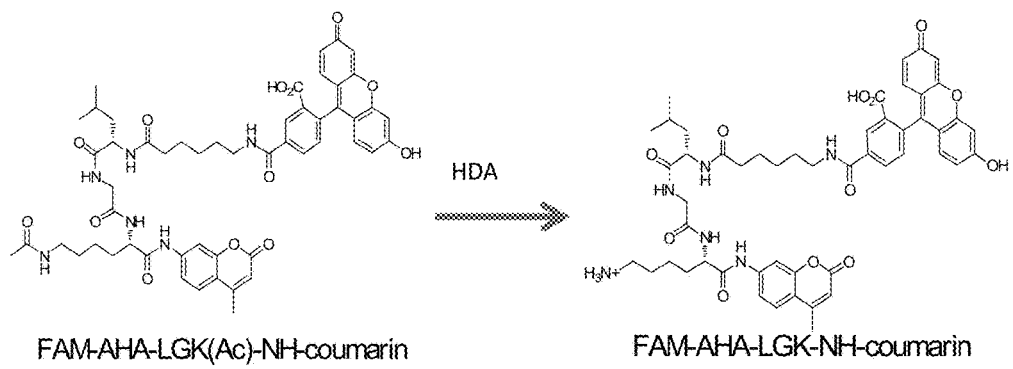
FIG. 8: Schematic diagram showing the use of microfluidic mobility shift assay to determine substrate modification via charged based separation of substrate from product, where an HDAC enzyme deacetylates an acetylated-lysine-containing substrate.
Figure 8:
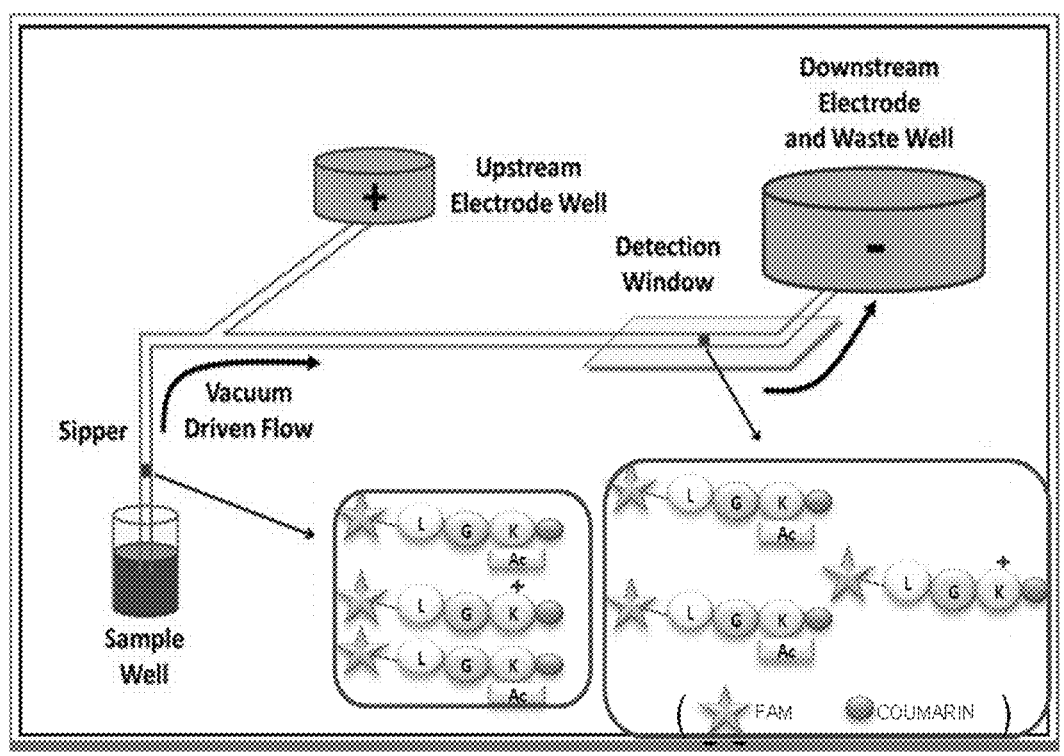

The kinetics of the inhibition of HDAC1 with SAHA or CI-994 was measured with Broad Substrate A on Caliper EZ reader II system. To establish the time-dependent mechanism of inhibition, the progress curves for HDAC1 in the presence of increasing concentrations of inhibitor SAHA or CI-994 were monitored for 4 hours. To test the reversibility of SAHA or CI-994, HDAC1 at 100-fold its final assay concentration (100 nM) and inhibitor at 10~20 fold its IC$_{50}$ after 1 h preincubation was diluted 100-fold with assay buffer containing 2 μM Broad Substrate A. Substrate conversion was monitored continuously on EZ reader II. Kinetic parameters (kon, koff) were derived from slow binding equations known in the art (See e.g., Chou C. J., et al., *J. Biol. Chem.*, 2008, 283, 35402-35409). SAHA was determined to be a fast on/fast off inhibitor for HDAC1 (FIG. 6) and CI-994 was determined to be a slow on/slow off inhibitor for HDAC1 (FIG. 7). The table below shows a summary of the kinetic parameters for SAHA and CI-994:

|  | Kinetic Parameters Summary | CI-994 | SAHA |
| --- | --- | --- | --- |
| HDAC1 | Kon(min-1, μM-1) | 0.25 |  |
|  | Koff(min-1) | 0.0094 | >0.2 |
|  | T(½) min | 74 | <4 |
|  | Ki(nM) | 37 | ~1.9** |
|  | IC50(nM) @3 hr | 46 | 5 |

**Ki was estimated from HDAC1 stability in the presence of SAHA

Structures of the reference compounds are given below:

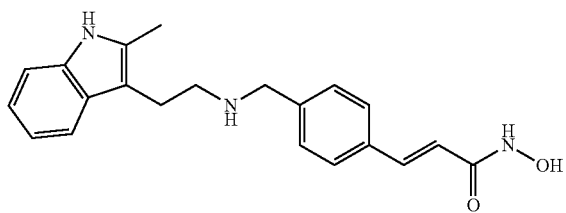

LBH-589 (Panobinostat)

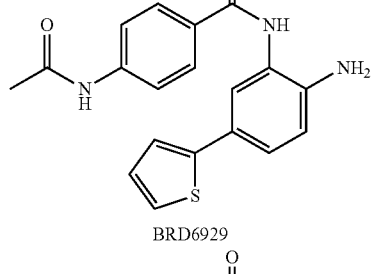

BRD6929

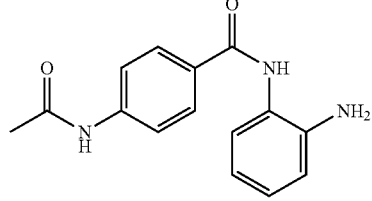

CI-994

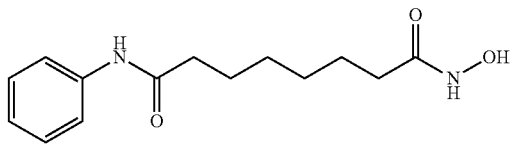

SAHA

The above reference compounds are discussed in Wilson A. J.; Holson, E.; Wagner, F.; Zhang, Y.-L.; Fass, D. M.; Haggarty, S. J.; Bhaskara, S.; Hiebert, S. W.; Schreiber, S. L.; Khabele, D. Cancer Biology & Therapy, 2011, Volume 12 Issue 6, 1-10: "The DNA damage mark pH2AX differentiates the cytotoxic effects of small molecule HDAC inhibitors in ovarian cancer cells".

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of Formula I or a salt thereof:

$$F_1-X_1-L_1-X_2-P_1-X_3-G_1 \quad \text{(Formula I);}$$

wherein:

$F_1$ is a fluorophore;

$L_1$ is alkylene, substituted alkylene, alkenylene, substituted alkenylene, alkynylene, or substituted alkynylene;

$P_1$ is a peptide containing a lysine residue, wherein the peptide can act as a substrate of a lysine deacetylase;

$G_1$ is coumarin, methyl coumarin, or N-methyl-3-phenyl-propanamide;

each of $X_1$, $X_2$, and $X_3$ is independently a direct bond, —O—, —S—, —C(O)—, —C(O)—$NR_{100}$—, —C(S)—, —C(S)—$NR_{100}$—, —C(O)O—, —$NR_{100}$— and —S(O)$_2$—; and each $R_{100}$ is independently hydrogen, alkyl, substituted alkyl, aryl or substituted aryl.

2. The compound according to claim 1, wherein $F_1$ is a fluorescein-based fluorophore.

3. The compound according to claim 2, wherein $F_1$ is 6-carboxy fluorescein (6-FAM), 5-carboxy fluorescein (5-FAM), or fluorescein isothiocyanate (FITC).

4. The compound according to claim 1, wherein $L_1$ is a $C_1$-$C_{10}$ alkylene group.

5. The compound according to claim 1, wherein $P_1$ is LGK(Ac), TGGK(Ac)APR (SEQ ID NO: 4), LGKGGAK(Ac) (SEQ ID NO: 5), TSPQPKK(Ac) (SEQ ID NO: 6), SPQPKK(Ac) (SEQ ID NO: 7), PQPKK(Ac) (SEQ ID NO: 8), TSRHK(Ac) (SEQ ID NO: 9), RGK(Ac), LGK(COCF$_3$), TGGK(COCF$_3$)APR (SEQ ID NO: 10), LGKGGAK(COCF$_3$) (SEQ ID NO: 11), TSPQPKK(COCF$_3$) (SEQ ID NO: 12), SPQPKK(COCF$_3$) (SEQ ID NO: 13), PQPKK(COCF$_3$) (SEQ ID NO: 14), TSRHK(COCF$_3$) (SEQ ID NO: 15), RGK(COCF$_3$), RHKK(Ac) (SEQ ID NO: 16), QPKK(Ac) (SEQ ID NO: 17), RHKK(COCF$_3$) (SEQ ID NO: 18), QPKK(COCF$_3$) (SEQ ID NO: 19), RHKK (SEQ ID NO: 20), QPKK (SEQ ID NO: 21), LGK, TGGKAPR (SEQ ID NO: 22), LGKGGAK (SEQ ID NO: 23), TSPQPKK (SEQ ID NO: 24), SPQPKK (SEQ ID NO: 25), PQPKK (SEQ ID NO: 26), TSRHK (SEQ ID NO: 27) or RGK.

6. The compound according to claim 1, wherein $X_1$ is selected from —O—, —C(O)NH—, —C(O)— and —C(O)O—.

7. The compound according to claim 1, wherein $X_2$ is selected from —O—, —C(O)NH—, —C(O)— and —C(O)O—.

8. The compound according to claim 1, wherein $X_3$ is selected from —O—, —C(O)NH—, —C(O)— and —C(O)O—.
9. The compound according to claim 1, wherein $F_1$ is selected from Table A:
TABLE A
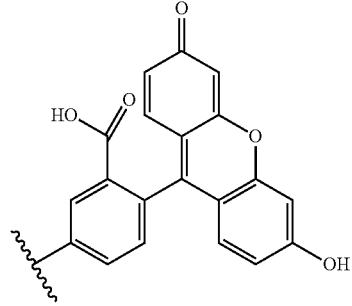 [SMILES: *c1ccc(-c2c3ccc(=O)cc-3oc3cc(O)ccc23)c(C(=O)O)c1]
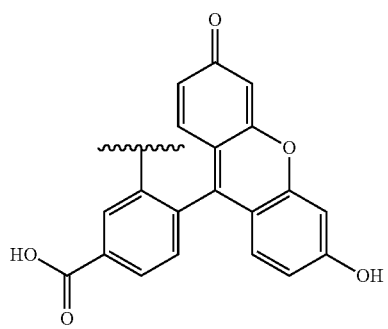 [SMILES: *c1cc(C(=O)O)ccc1-c1c2ccc(=O)cc-2oc2cc(O)ccc12]
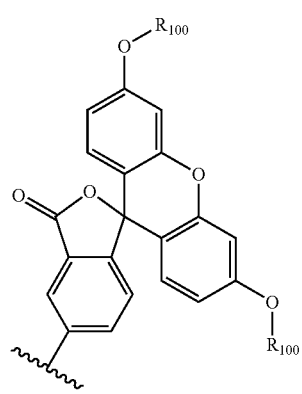
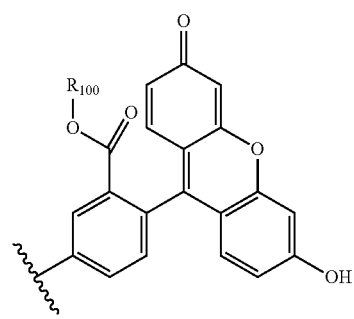
TABLE A-continued
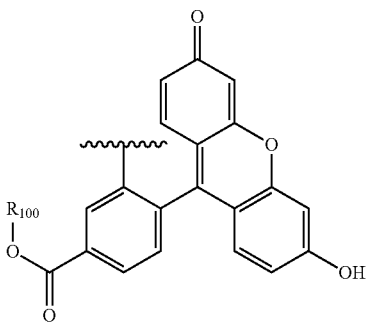
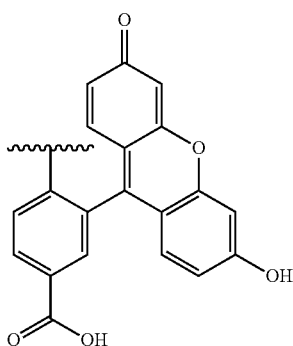 [SMILES: *c1ccc(C(=O)O)cc1-c1c2ccc(=O)cc-2oc2cc(O)ccc12]
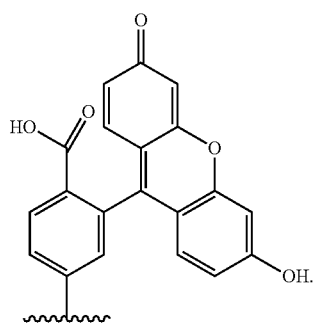 [SMILES: *c1ccc(C(=O)O)c(-c2c3ccc(=O)cc-3oc3cc(O)ccc23)c1]
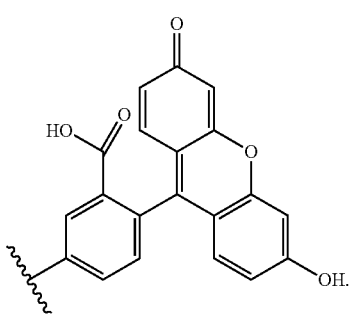 [SMILES: *c1ccc(-c2c3ccc(=O)cc-3oc3cc(O)ccc23)c(C(=O)O)c1]
10. The compound of claim 9, wherein $F_1$ is
11. The compound of claim 10, wherein $P_1$ is selected from the group consisting of:

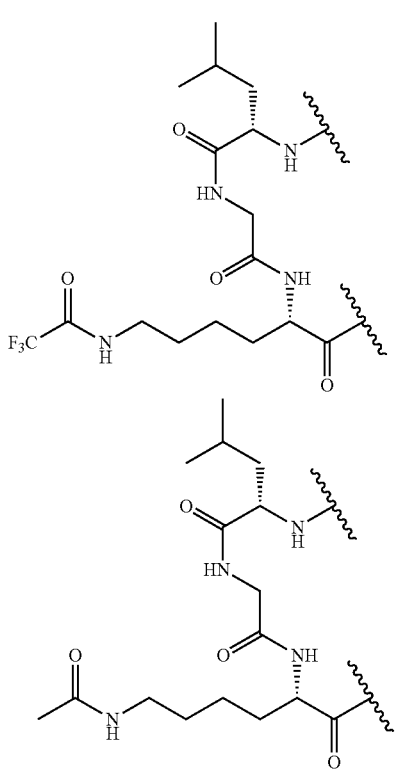
and
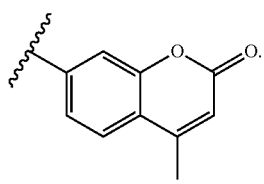 [SMILES: *c1ccc2c(C)cc(=O)oc2c1]
12. The compound of claim 11, wherein $G_1$ is coumarin or methyl coumarin.
13. The compound of claim 12, wherein $G_1$ is
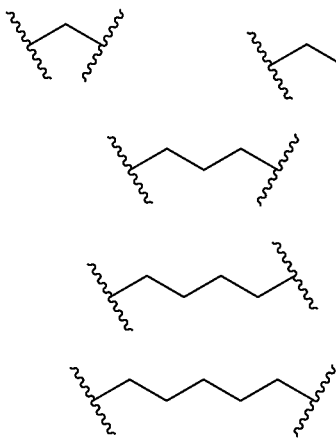
14. The compound according to claim 1, wherein $L_1$ is selected from Table B:
TABLE B
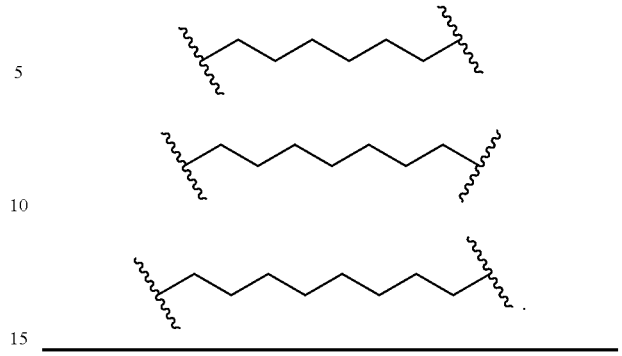
TABLE B-continued
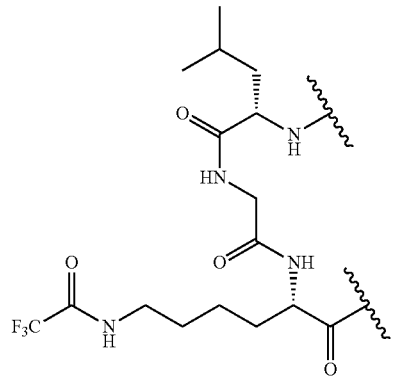 [SMILES: *N[C@@H](CC(C)C)C(=O)NCC(=O)N[C@@H](CCCCNC(=O)C(F)(F)F)C(*)=O]
15. The compound according to claim 1, wherein $P_1$ is selected from Table C:
TABLE C
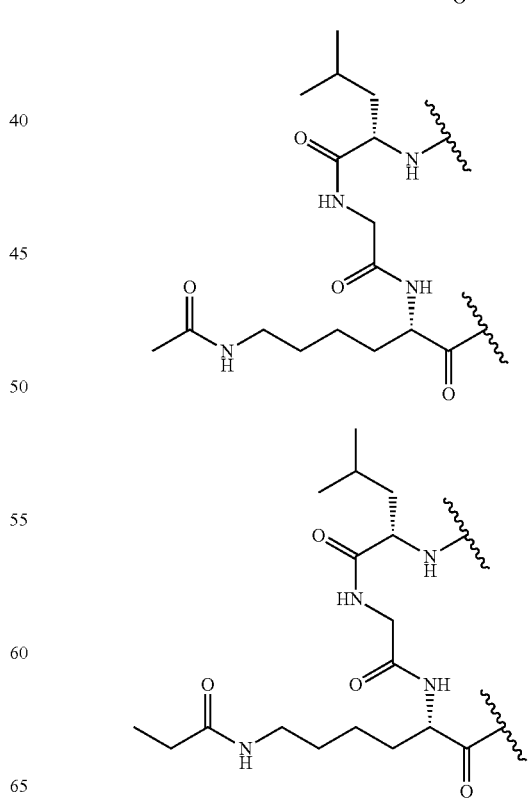

TABLE C-continued
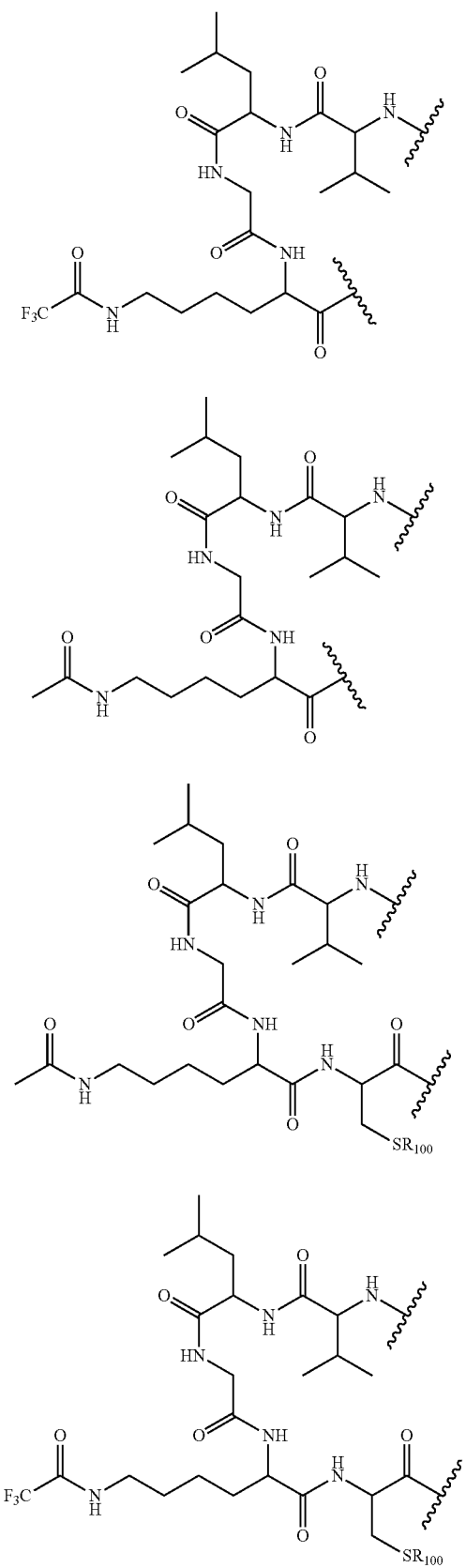
TABLE C-continued
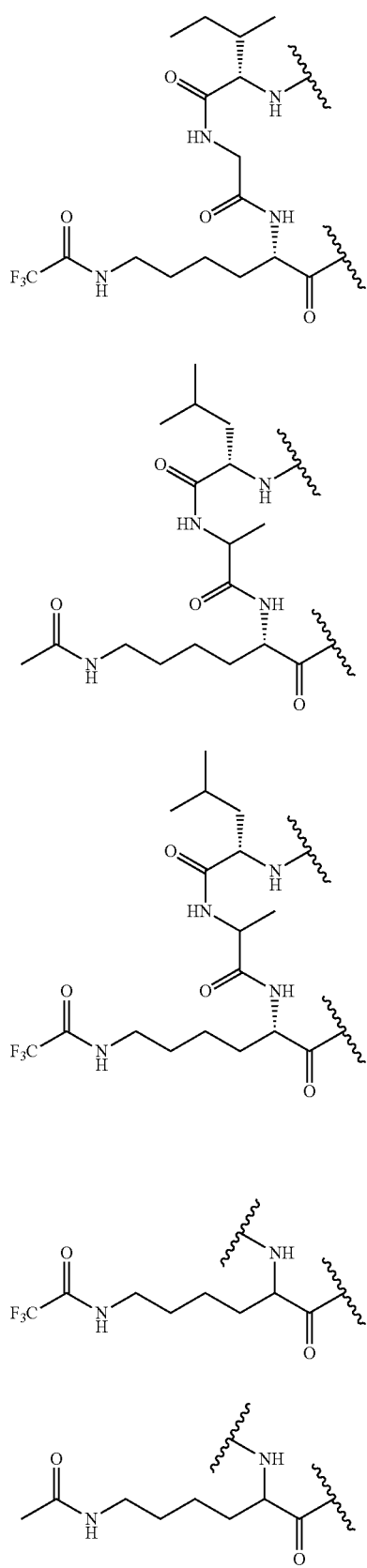

TABLE C-continued
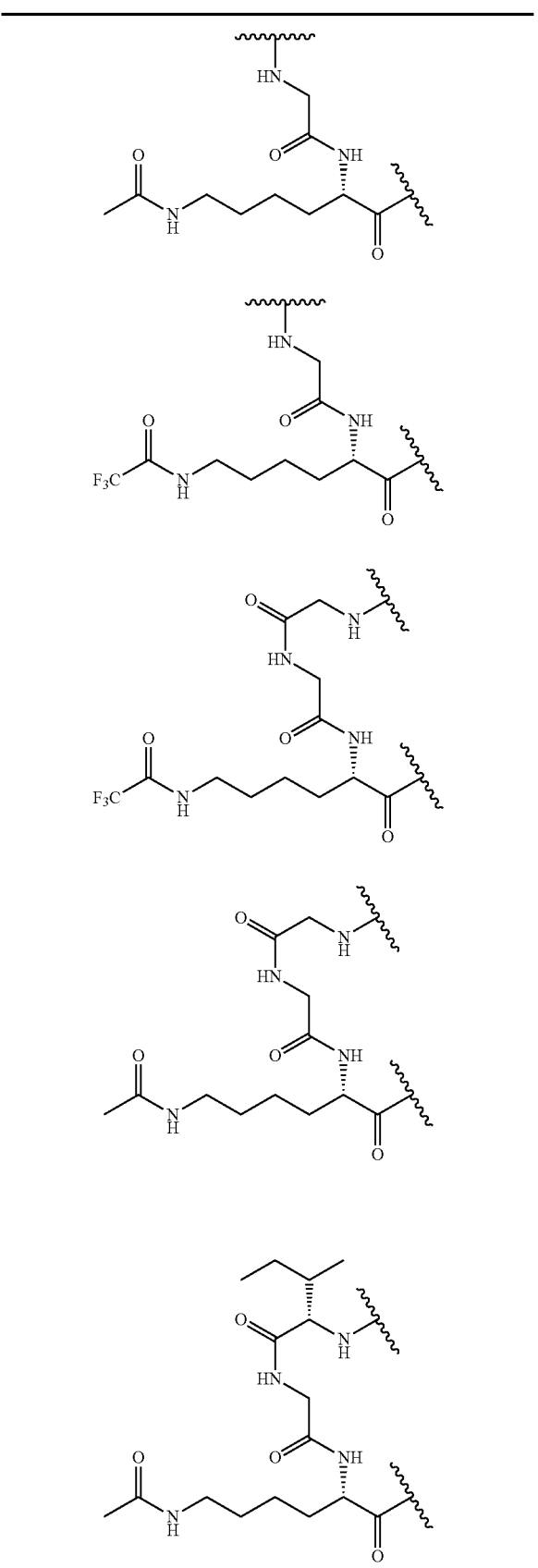
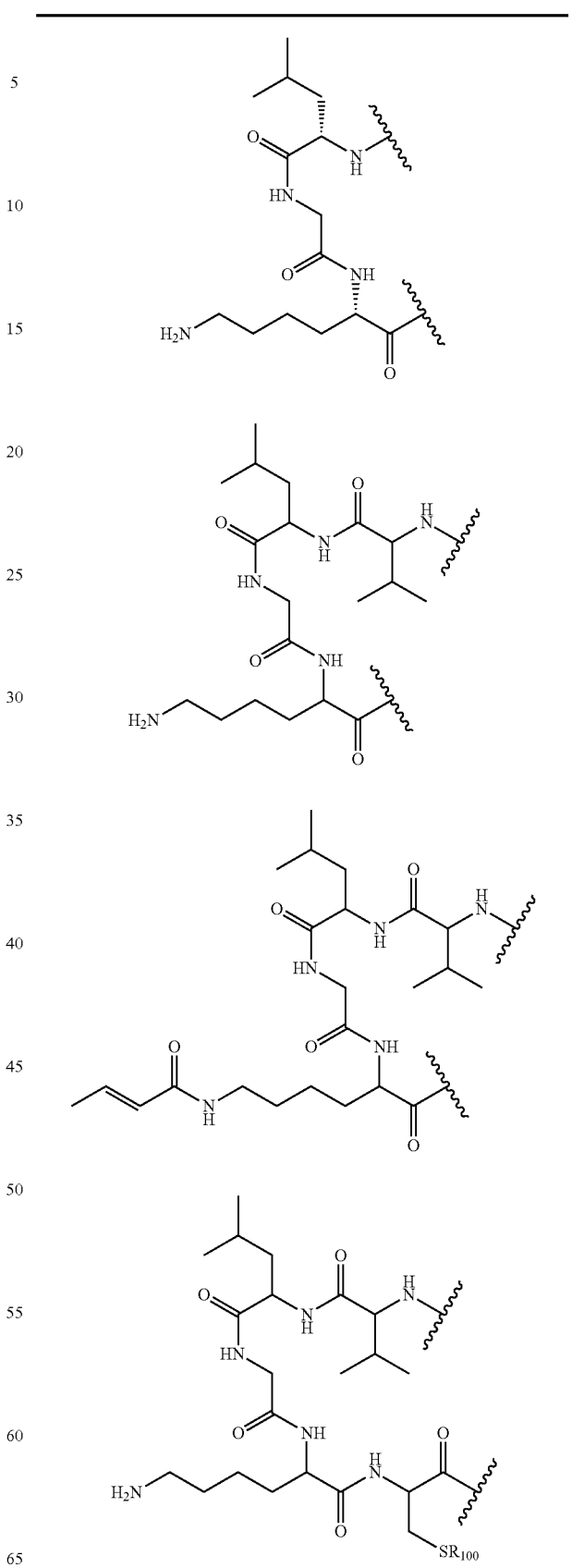

TABLE C-continued
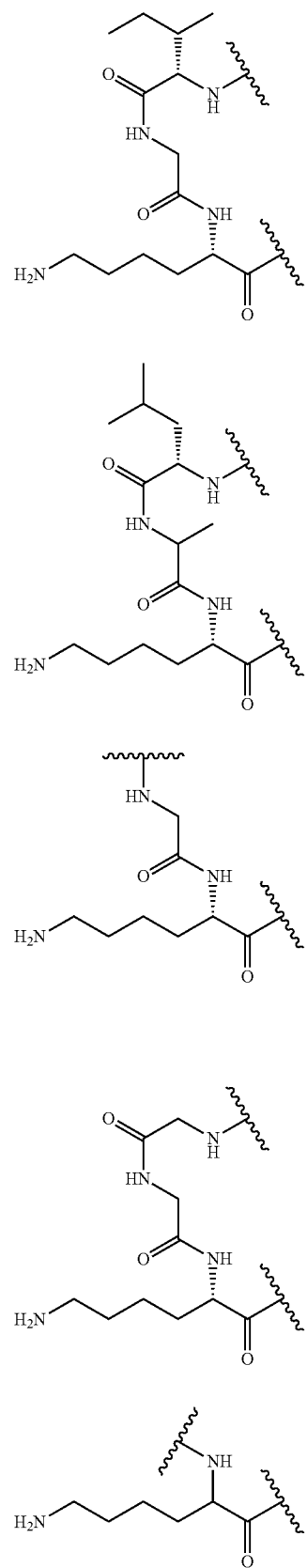
TABLE C-continued
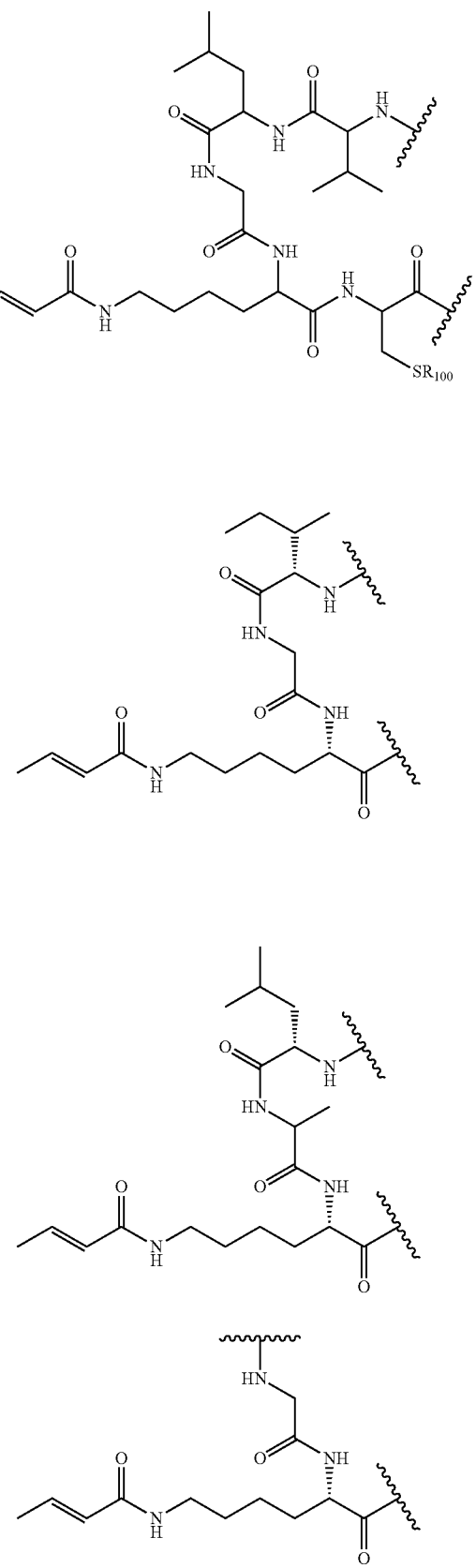

TABLE C-continued
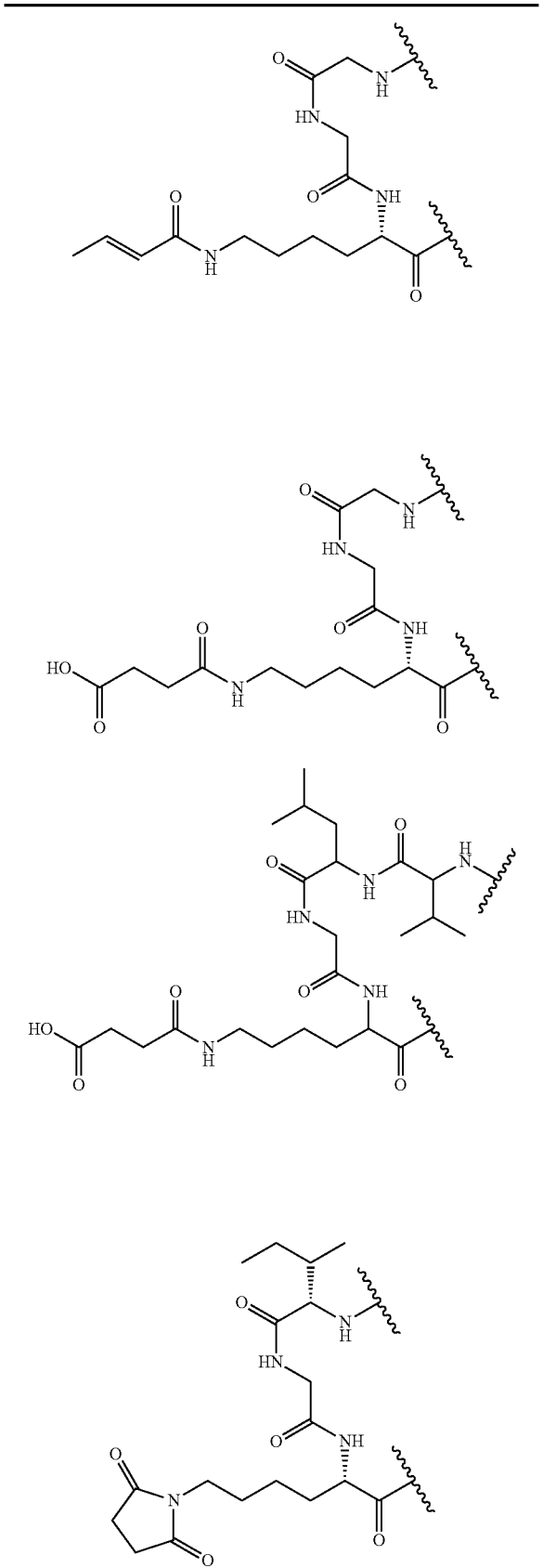
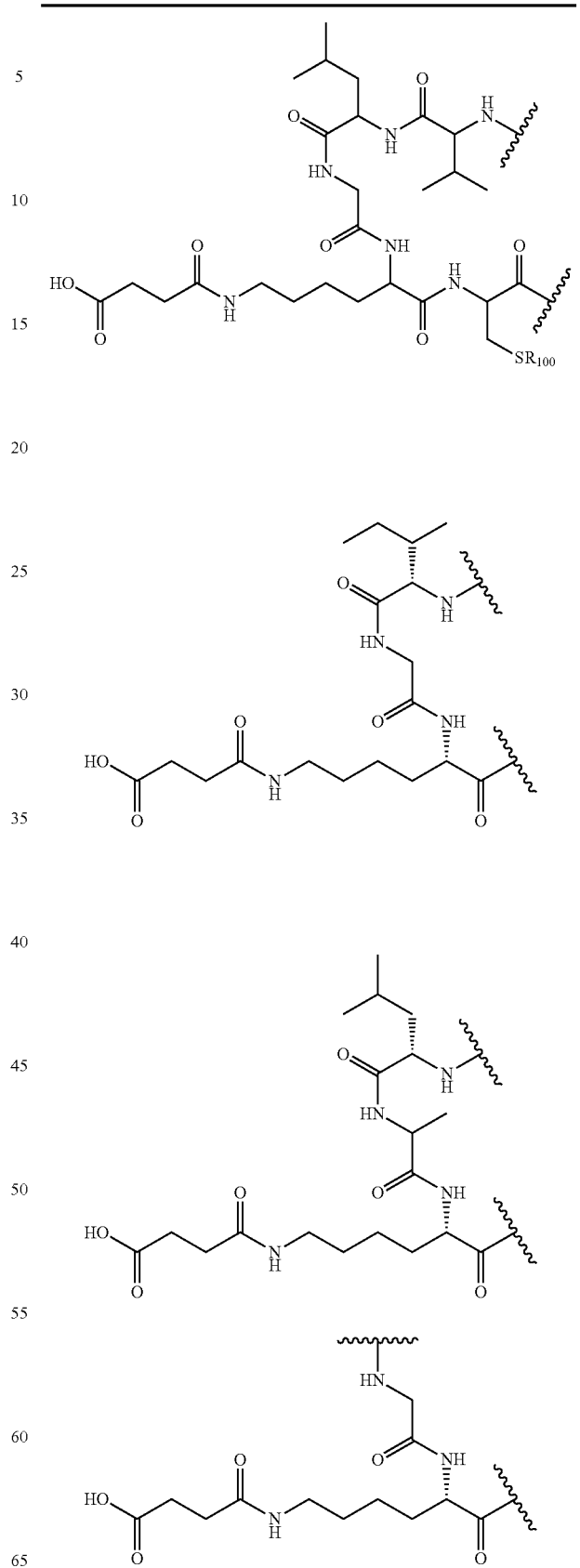

TABLE C-continued
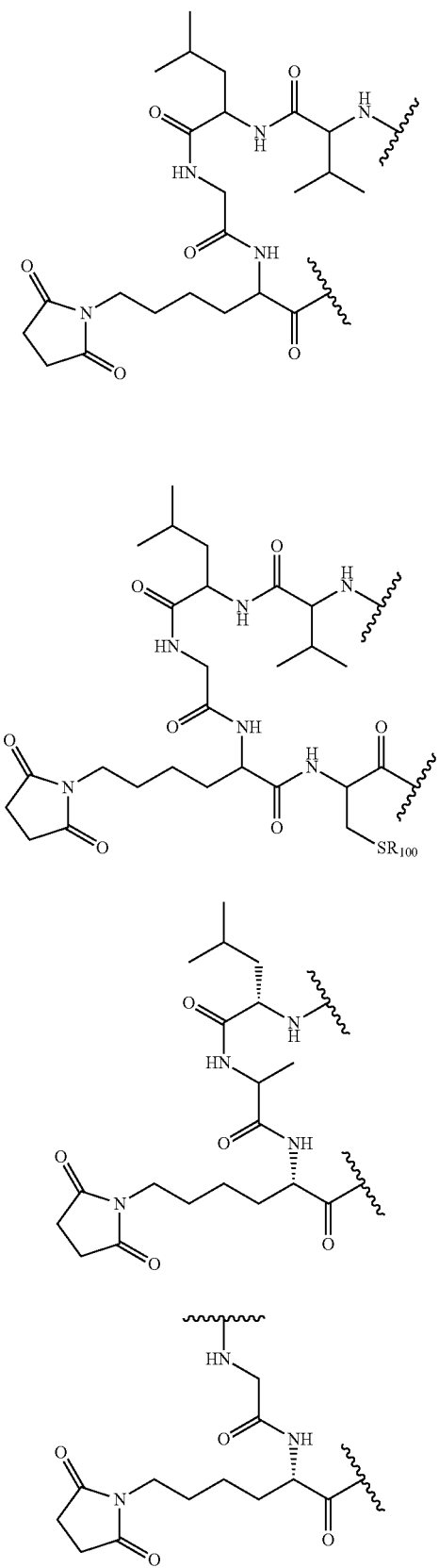
TABLE C-continued
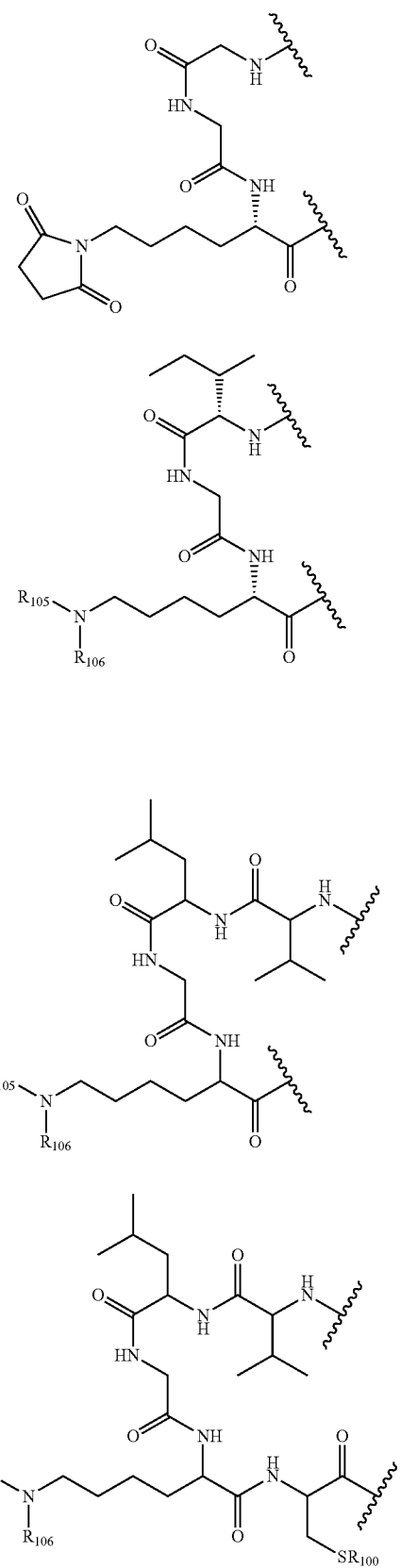

TABLE C-continued
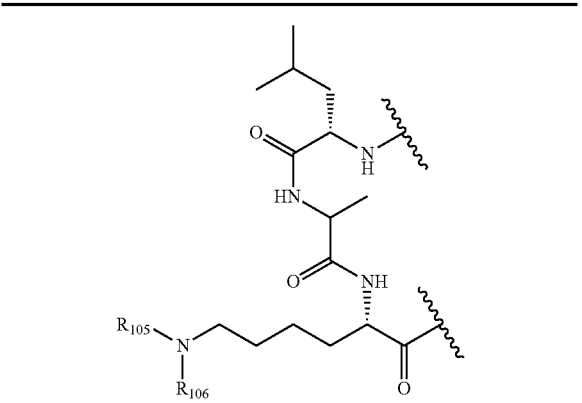
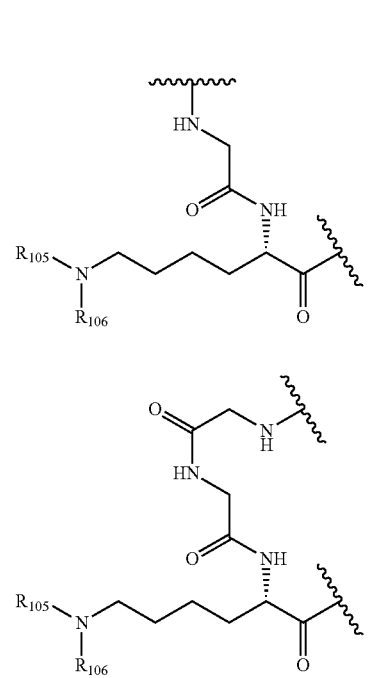
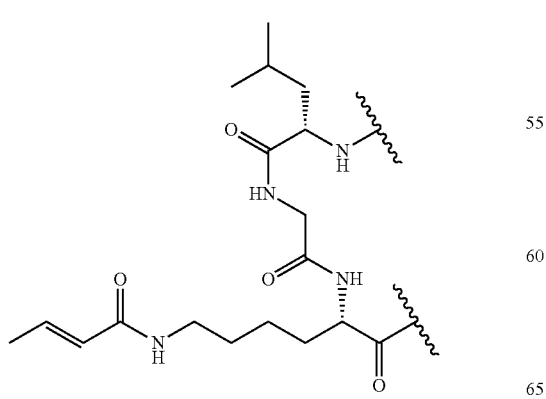
TABLE C-continued
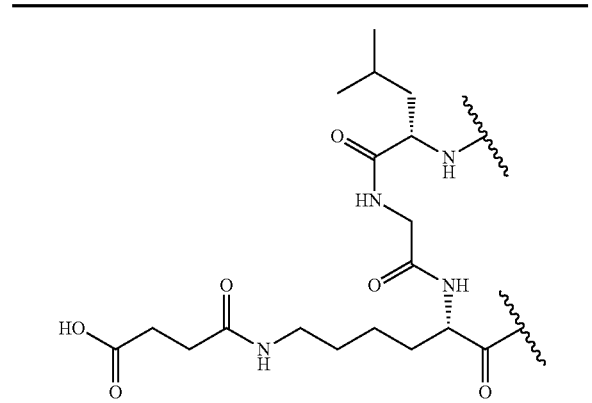
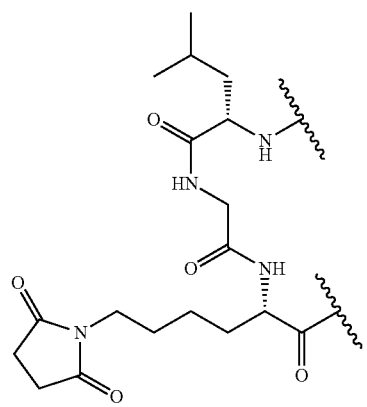 [SMILES: *N[C@@H](CC(C)C)C(=O)NCC(=O)N[C@@H](CCCCN1C(=O)CCC1=O)C(*)=O]
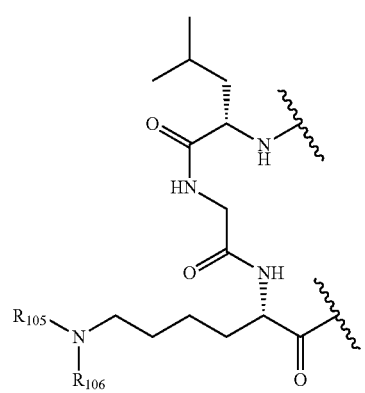

TABLE C-continued

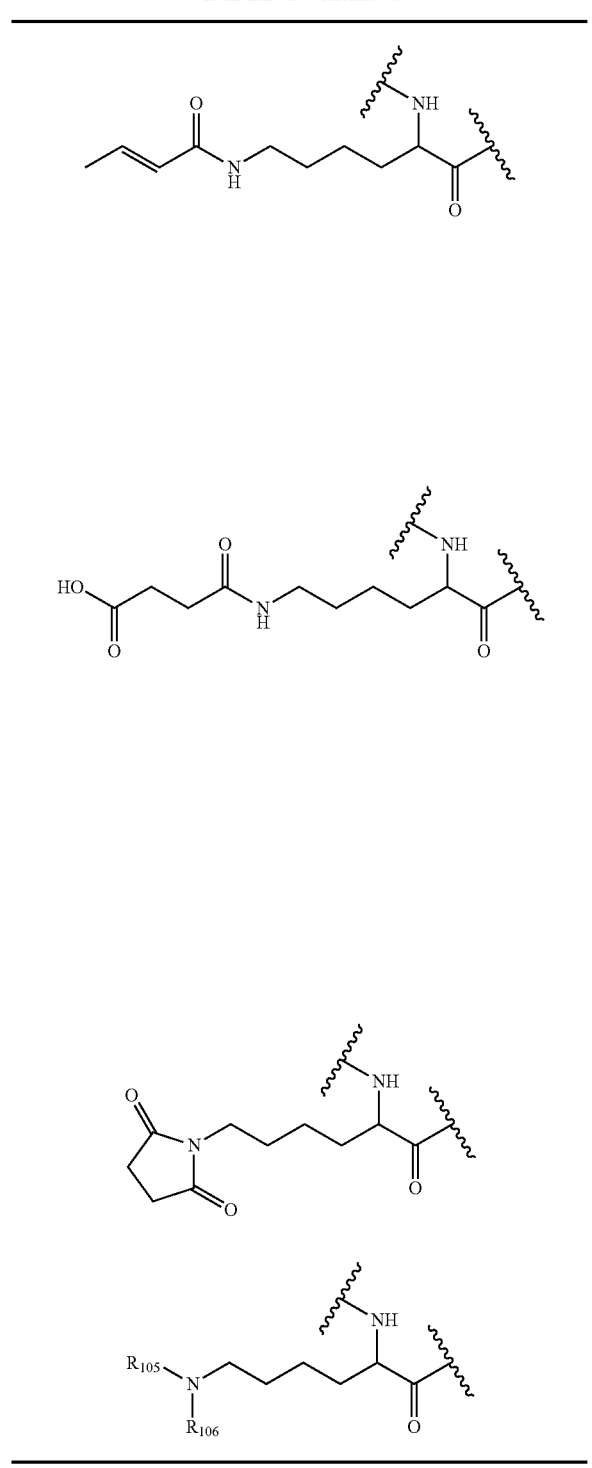

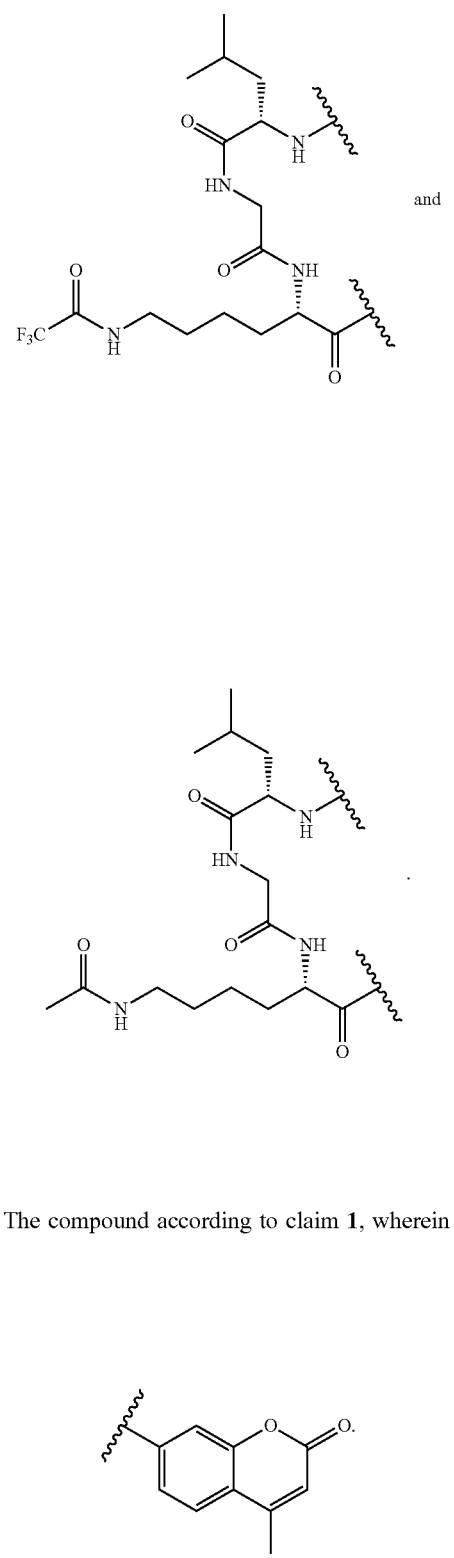

wherein each $R_{105}$ and $R_{106}$ is independently hydrogen, —C(O)—$C_1$-$C_6$ alkyl, —C(S)—$C_1$-$C_6$ alkyl, —C(O)-substituted $C_1$-$C_6$ alkyl, —C(S)-substituted $C_1$-$C_6$ alkyl, C(O)-aryl, —C(S)-aryl, —C(O)-substituted aryl, —C(S)-substituted aryl, —S(O)—$C_1$-$C_6$ alkyl, —S(O)$_2$—$C_1$-$C_6$ alkyl, alkyl, substituted $C_1$-$C_6$ alkyl, aryl or substituted aryl.

16. The compound of claim 15, wherein $P_1$ is selected from the group consisting of:

17. The compound according to claim 1, wherein $G_1$ is

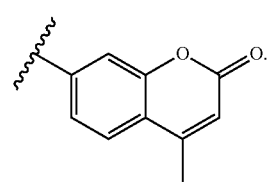 [SMILES: *c1ccc2c(C)cc(=O)oc2c1]

18. The compound of claim 1, wherein the lysine residue of $P_1$ is acetylated or trifluoroacetylated.

19. A compound selected from Table E or a salt thereof:
TABLE E
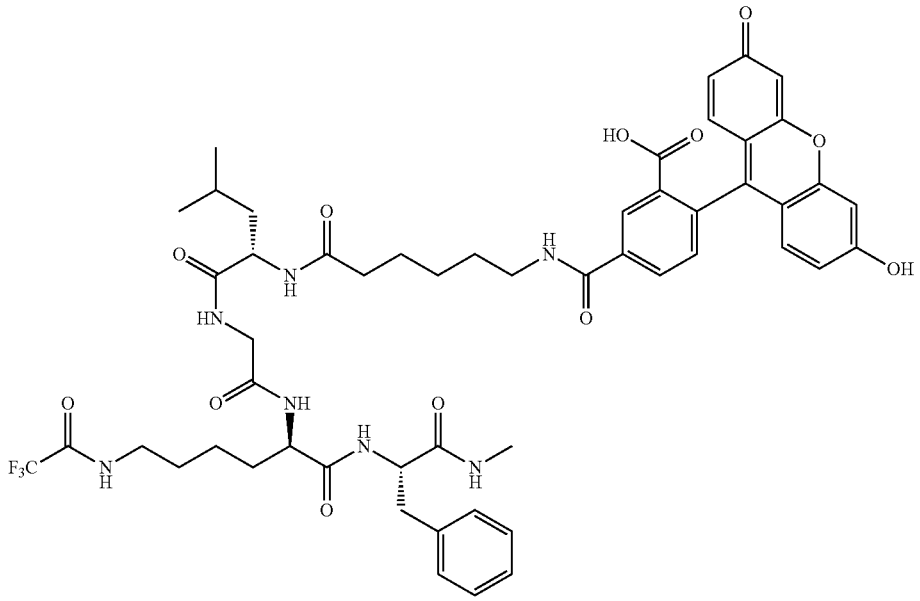 [SMILES: CNC(=O)[C@H](Cc1ccccc1)NC(=O)[C@@H](CCCCNC(=O)C(F)(F)F)NC(=O)CNC(=O)[C@H](CC(C)C)NC(=O)CCCCCNC(=O)c1ccc(-c2c3ccc(=O)cc-3oc3cc(O)ccc23)c(C(=O)O)c1]
Broad Substrate D
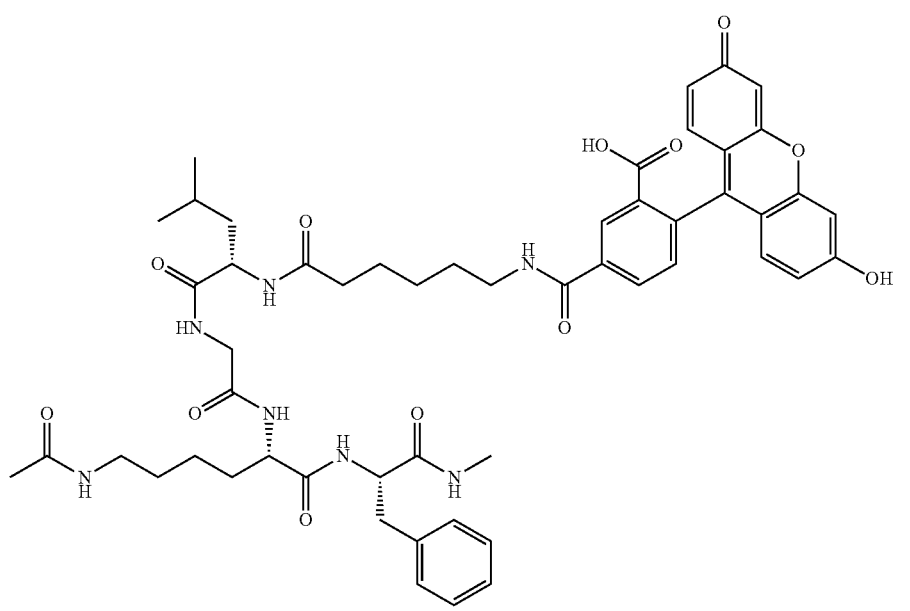 [SMILES: CNC(=O)[C@H](Cc1ccccc1)NC(=O)[C@H](CCCCNC(C)=O)NC(=O)CNC(=O)[C@H](CC(C)C)NC(=O)CCCCCNC(=O)c1ccc(-c2c3ccc(=O)cc-3oc3cc(O)ccc23)c(C(=O)O)c1]
Broad Substrate C TABLE E-continued

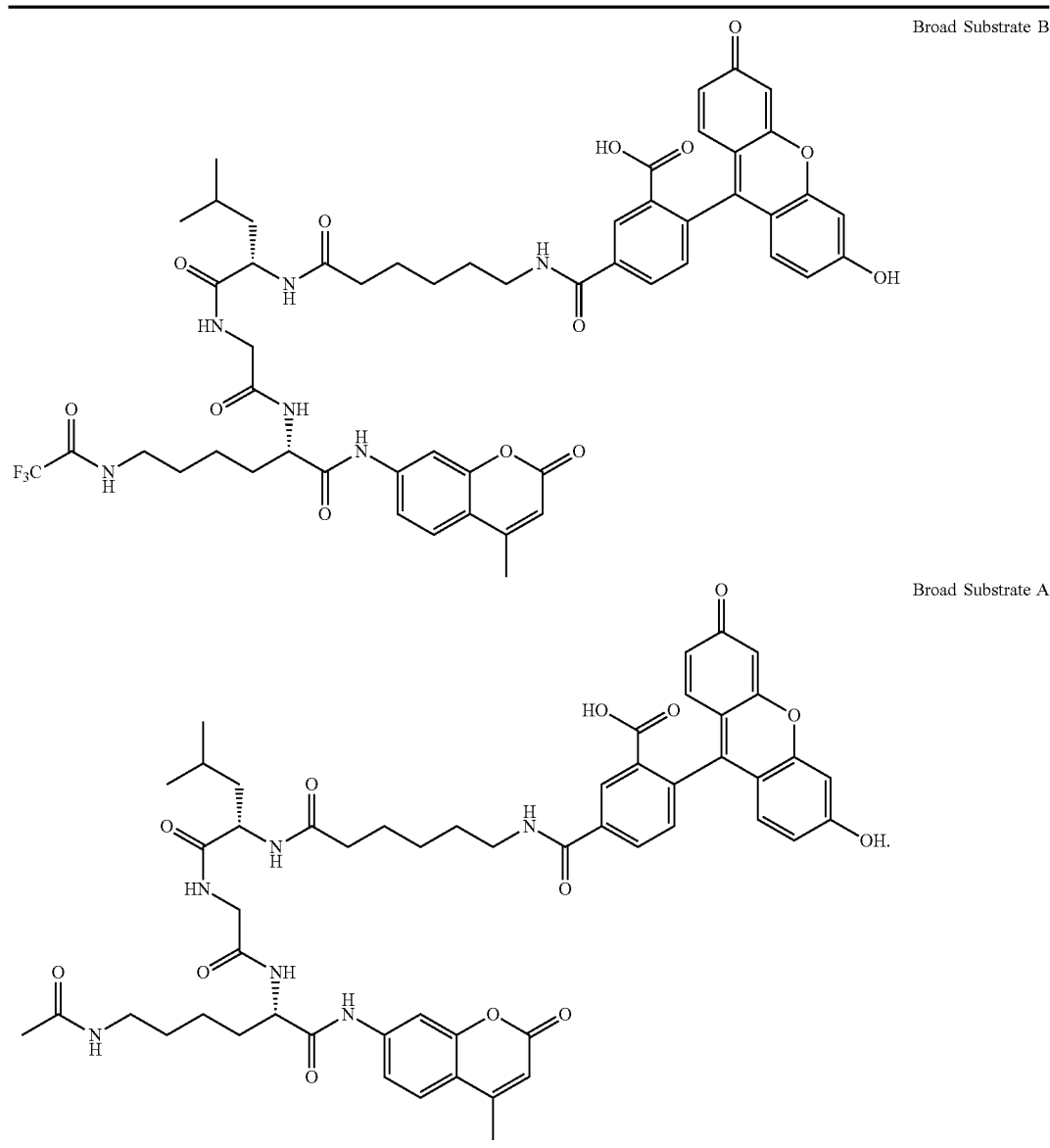

20. A method for determining lysine deacetylase activity comprising the step of incubating a lysine deacetylase with a compound according to claim 1 and monitoring the modification of a lysine residue of said compound over time.

21. The method according to claim 20, wherein said step of monitoring the modification of a lysine residue of said compound comprises the step of monitoring the fluorescence of said compound or the product resulting from the modification the lysine residue.

22. The method according to claim 21, wherein the modification of the lysine residue is deacetylation of an acetylated lysine residue or detrifluoroacetylation of a trifluoroacetylated lysine residue.

23. The method according to claim 20, wherein said step of monitoring the modification of the lysine residue over time comprises separating the product of resulting from the modification of the lysine residue from the compound using a microfluidic mobility shift technology.

24. A method for determining histone deacetylase (HDAC) activity comprising the step of incubating an HDAC with a compound according to claim 1 and determining the activity of the HDAC enzyme.

25. The method according to claim 24, wherein said HDAC is an isoform of HDAC selected from 1, 2, 3, 4, 5, 6, 7, 8, 9, 10, 11 or SIRT 1, 2, 3, 4, 5, 6 or 7.

26. The method according to claim 24, wherein said step of determining the activity of the HDAC enzyme comprises the monitoring of the release of $G_1$.

27. A method for determining histone acetyltransferase activity comprising the step of incubating a histone acetyl transferase with a compound according to claim 1 and monitoring the modification of a lysine residue of said compound over time.

28. The method according to claim 27, wherein said step of determining the activity of the histone acetyltransferase enzyme comprises the step of monitoring the fluorescence of the compound or the product of the modification of the lysine residue.

29. The method according to claim 27, wherein said step of determining the activity of the histone acetyltransferase enzyme comprises the monitoring of the release of $G_1$.

* * * * *

```
                              SEQUENCE LISTING

<160> NUMBER OF SEQ ID NOS: 29

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(4)
<223> OTHER INFORMATION: absent or a natural or unnatrural amino acid

<400> SEQUENCE: 1

Xaa Xaa Xaa Xaa Lys
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(4)
<223> OTHER INFORMATION: absent or a natural or unnatrural amino acid
<220> FEATURE:
<221> NAME/KEY: MOD_RES
<222> LOCATION: (5)..(5)
<223> OTHER INFORMATION: Ac = Lys

<400> SEQUENCE: 2
```

```
Xaa Xaa Xaa Xaa Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(4)
<223> OTHER INFORMATION: absent or a natural or unnatrural amino acid
<220> FEATURE:
<221> NAME/KEY: MOD_RES
<222> LOCATION: (5)..(5)
<223> OTHER INFORMATION: COCF3 = Lys

<400> SEQUENCE: 3

Xaa Xaa Xaa Xaa Lys
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: Ac = Lys

<400> SEQUENCE: 4

Thr Gly Gly Lys Ala Pro Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: Ac- Lys
<220> FEATURE:
<221> NAME/KEY: MOD_RES
<222> LOCATION: (7)..(7)
<223> OTHER INFORMATION: Ac- Lys

<400> SEQUENCE: 5

Leu Gly Lys Gly Gly Ala Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (6)..(7)
<223> OTHER INFORMATION: Ac = Lys

<400> SEQUENCE: 6

Thr Ser Pro Gln Pro Lys Lys
1               5
```

<210> SEQ ID NO 7
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(6)
<223> OTHER INFORMATION: Ac = Lys

<400> SEQUENCE: 7

Ser Pro Gln Pro Lys Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(5)
<223> OTHER INFORMATION: Ac = Lys

<400> SEQUENCE: 8

Pro Gln Pro Lys Lys
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: Ac = Lys

<400> SEQUENCE: 9

Thr Ser Arg His Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: COCF3 = Lys

<400> SEQUENCE: 10

Thr Gly Gly Lys Ala Pro Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(3)

```
<223> OTHER INFORMATION: COCF3 = Lys
<220> FEATURE:
<221> NAME/KEY: MOD_RES
<222> LOCATION: (7)..(7)
<223> OTHER INFORMATION: COCF3 = Lys

<400> SEQUENCE: 11

Leu Gly Lys Gly Gly Ala Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (6)..(7)
<223> OTHER INFORMATION: COCF3 = Lys

<400> SEQUENCE: 12

Thr Ser Pro Gln Pro Lys Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(6)
<223> OTHER INFORMATION: COCF3 = Lys

<400> SEQUENCE: 13

Ser Pro Gln Pro Lys Lys
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(5)
<223> OTHER INFORMATION: COCF3 = Lys

<400> SEQUENCE: 14

Pro Gln Pro Lys Lys
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: COCF3 = Lys

<400> SEQUENCE: 15

Thr Ser Arg His Lys
1               5
```

```
<210> SEQ ID NO 16
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(4)
<223> OTHER INFORMATION: Ac = Lys

<400> SEQUENCE: 16

Arg His Lys Lys
1

<210> SEQ ID NO 17
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(4)
<223> OTHER INFORMATION: Ac = Lys

<400> SEQUENCE: 17

Gln Pro Lys Lys
1

<210> SEQ ID NO 18
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(4)
<223> OTHER INFORMATION: COCF3 = Lys

<400> SEQUENCE: 18

Arg His Lys Lys
1

<210> SEQ ID NO 19
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(4)
<223> OTHER INFORMATION: COCF3 = Lys
<220> FEATURE:
<221> NAME/KEY: MOD_RES
<222> LOCATION: (3)..(4)
<223> OTHER INFORMATION: COCF3 = Lys

<400> SEQUENCE: 19

Gln Pro Lys Lys
1

<210> SEQ ID NO 20
<211> LENGTH: 4
<212> TYPE: PRT
<213> ORGANISM: Artificial Sequence
<220> FEATURE:
<223> OTHER INFORMATION: Synthetic Peptide
```

<400> SEQUENCE: 20

Arg His Lys Lys
1

<210> SEQ ID NO 21
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 21

Gln Pro Lys Lys
1

<210> SEQ ID NO 22
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 22

Thr Gly Gly Lys Ala Pro Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 23

Leu Gly Lys Gly Gly Ala Lys
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 24

Thr Ser Pro Gln Pro Lys Lys
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 25

Ser Pro Gln Pro Lys Lys
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide

```
<400> SEQUENCE: 26

Pro Gln Pro Lys Lys
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 27

Thr Ser Arg His Lys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (9)..(9)
<223> OTHER INFORMATION: Ac = Lys

<400> SEQUENCE: 28

Phe Ala Met Ala His Ala Leu Gly Lys
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 29

Phe Ala Met Ala His Ala Leu Gly Lys
1               5
```